United States Patent
Ariad et al.

(10) Patent No.: US 12,322,509 B2
(45) Date of Patent: Jun. 3, 2025

(54) METHODS AND RELATED ASPECTS FOR ANALYZING CHROMOSOME NUMBER STATUS

(71) Applicant: THE JOHNS HOPKINS UNIVERSITY, Baltimore, MD (US)

(72) Inventors: Daniel Ariad, Pikesville, MD (US); Rajiv McCoy, Baltimore, MD (US); Manuel Viotti, San Francisco, CA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 18/035,811

(22) PCT Filed: Nov. 5, 2021

(86) PCT No.: PCT/US2021/058219
§ 371 (c)(1),
(2) Date: May 8, 2023

(87) PCT Pub. No.: WO2022/098980
PCT Pub. Date: May 12, 2022

(65) Prior Publication Data
US 2023/0307130 A1    Sep. 28, 2023

Related U.S. Application Data

(60) Provisional application No. 63/190,033, filed on May 18, 2021, provisional application No. 63/111,037, filed on Nov. 8, 2020.

(51) Int. Cl.
*G16H 50/20* (2018.01)
*G16B 20/10* (2019.01)
*G16B 20/20* (2019.01)
*G16B 40/20* (2019.01)

(52) U.S. Cl.
CPC ............. *G16H 50/20* (2018.01); *G16B 20/10* (2019.02); *G16B 20/20* (2019.02); *G16B 40/20* (2019.02)

(58) Field of Classification Search
CPC ......... G16B 20/20; G16B 20/10; G16B 40/20
See application file for complete search history.

(56) References Cited

U.S. PATENT DOCUMENTS

| | | | | |
|---|---|---|---|---|
| 11,479,812 | B2* | 10/2022 | Kirkizlar | C12Q 1/6853 |
| 2010/0120045 | A1* | 5/2010 | Helgadottir | C12Q 1/6883 |
| | | | | 435/6.1 |
| 2011/0105353 | A1* | 5/2011 | Lo | G16B 20/20 |
| | | | | 506/9 |
| 2022/0233588 | A1* | 7/2022 | Sourdive | C12Q 1/6881 |
| 2023/0014607 | A1* | 1/2023 | Green | G16B 20/20 |

OTHER PUBLICATIONS

International Preliminary Report on Patentability in corresponding International Application No. PCT/US2021/058219 mailed on May 19, 2023, 8 pages.

(Continued)

*Primary Examiner* — Jay M. Patel
(74) *Attorney, Agent, or Firm* — MH2 Technology Law Group LLP

(57) ABSTRACT

Provided herein are methods of distinguishing between meiotic- and mitotic-origin aneuploidies in certain embodiments. Related systems and computer program products are also provided.

20 Claims, 21 Drawing Sheets

(56) References Cited

OTHER PUBLICATIONS

International Search Report and Written Opinion in corresponding International Application No. PCT/US2021/058219 mailed on Feb. 17, 2022, 10 pages.
Bisignano, A. et al. "PGD and aneuploidy screening for 24 chromosomes: advantages and disadvantages of competing platforms." Reproductive biomedicine online 23.6 (2011): 677-685.
Meena, Jagan Singh, et al. "Overview of emerging nonvolatile memory technologies." Nanoscale research letters 9 (2014): 1-33.

* cited by examiner

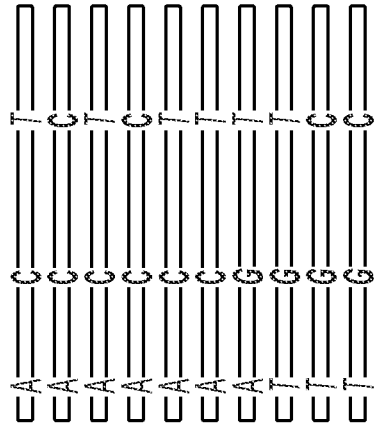

Within defined genomic windows, select reads overlapping informative SNPs that tag common haplotype variation

FIG. 4A

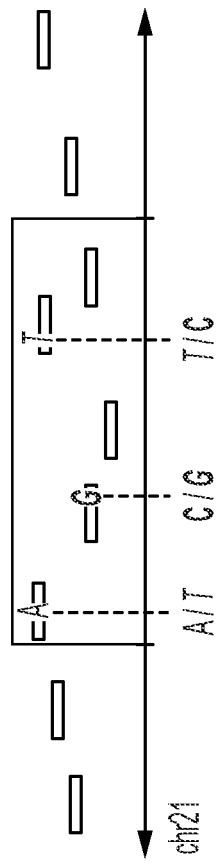

Obtain joint frequencies of corresponding SNPs from a phased panel of ancestry-matched reference haplotypes

FIG. 4B

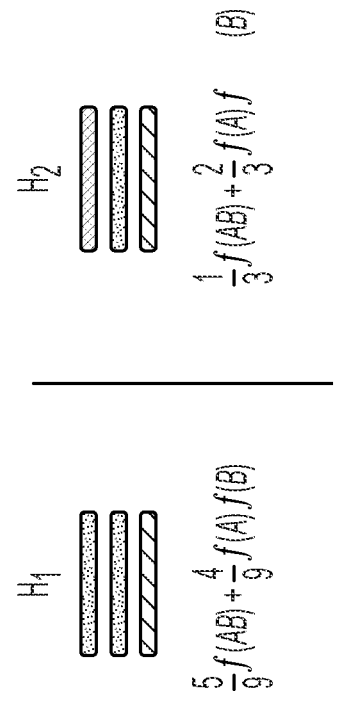

Randomly select 2-16 reads and compute probabilities of observed alleles under competing trisomy hypotheses

FIG. 4C

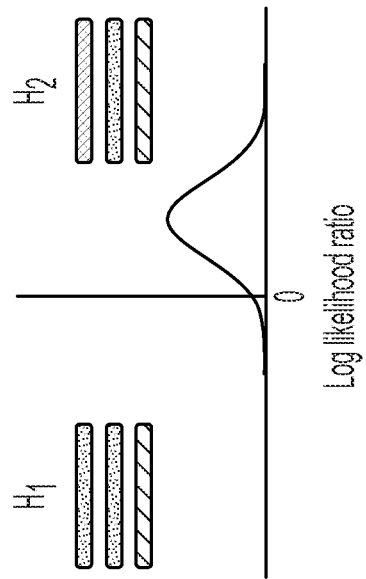

Compare the hypotheses by computing a likelihood ratio and estimate the mean and variance by sub-sampling random sets of reads using a bootstrapping approach

FIG. 4D

| number of reads | BPH | SPH |
|---|---|---|
| 2 | $P_{BPH}(A \wedge B) = \frac{1}{3} f(AB) + \frac{2}{3} f(A) f(B)$ | $P_{SPH}(A \wedge B) = \frac{5}{9} f(AB) + \frac{4}{9} f(A) f(B)$ |
| 3 | $P_{BPH}(A \wedge B \wedge C) = \frac{1}{9} f(ABC) + \frac{2}{9}(f(AB)f(C) + f(AC)f(B) + f(A)f(BC)) + f(A)f(B)f(C))$ | $P_{SPH}(A \wedge B \wedge C) = \frac{1}{3} f(ABC) + \frac{2}{9}(f(AB)f(C) + f(AC)f(B) + f(BC)f(A))$ |
| 4 | $P_{BPH}(A \wedge B \wedge C \wedge D) = \frac{1}{27} f(ABCD) + \frac{2}{27}(f(ABC)f(D) + f(ABD)f(C) + f(ACD)f(B) + f(BCD)f(A)) + f(A)f(B)f(C)f(D) + f(A)f(B)f(CD) + f(A)f(C)f(BD) + f(A)f(D)f(BC) + f(B)f(C)f(AD) + f(B)f(D)f(AC) + f(C)f(D)f(AB) + f(AB)f(CD) + f(AC)f(BD) + f(AD)f(BC))$ | $P_{SPH}(A \wedge B \wedge C \wedge D) = \frac{17}{81} f(ABCD) + \frac{10}{81}(f(ABC)f(D) + f(ABD)f(C) + f(ACD)f(B) + f(BCD)f(A)) + \frac{8}{81}(f(AB)f(CD) + f(AD)f(BC) + f(AC)f(BD))$ |

FIG. 8

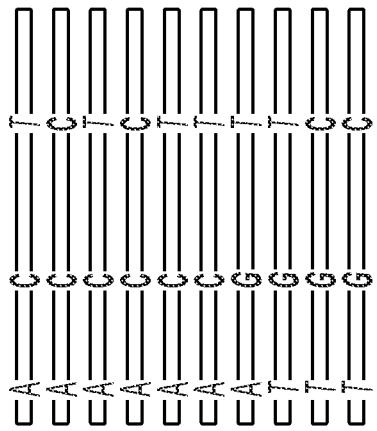

Within a defined genomic window, prioritize potentially informative reads that overlap with common SNPs

FIG. 10A

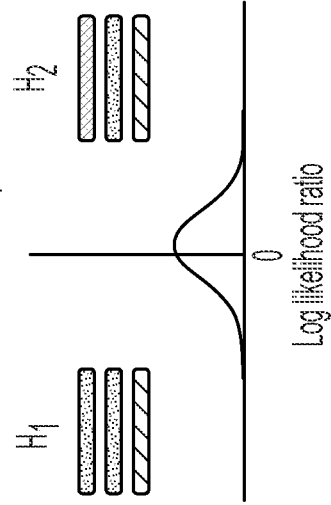

Quantify corresponding haplotype frequencies within a reference panel

FIG. 10B

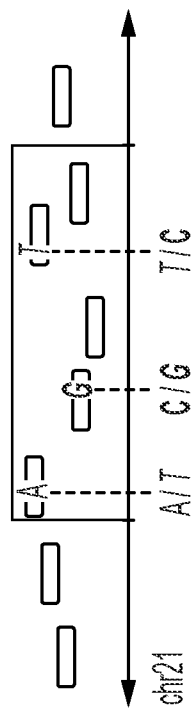

Randomly resample reads and compute likelihoods of observed alleles under competing ploidy hypotheses

FIG. 10C

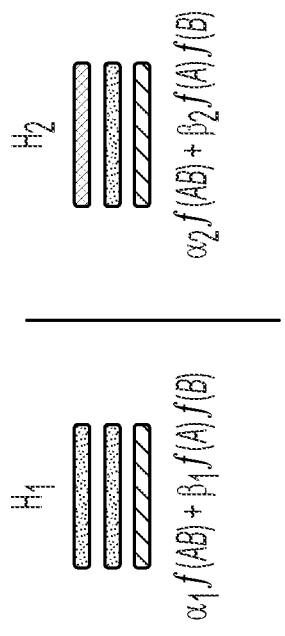

Compare with likelihood ratio and repeat step C multiple times to form a bootstrap distribution

FIG. 10D

METHODS AND RELATED ASPECTS FOR ANALYZING CHROMOSOME NUMBER STATUS

CROSS-REFERENCE TO RELATED APPLICATIONS

This application claims priority to U.S. Provisional Patent Application Ser. Nos. 63/190,033, filed May 18, 2021 and 63/111,037, filed Nov. 8, 2020, the disclosure of which is incorporated herein by reference.

STATEMENT OF GOVERNMENT SUPPORT

This invention was made with government support under grant GM133747 awarded by the National Institutes of Health. The government has certain rights in the invention.

BACKGROUND

Whole-chromosome gains and losses (aneuploidies), are extremely common in human embryos and are the leading cause of pregnancy loss and congenital disorders, both in the context of in vitro fertilization (IVF) and natural conception. Aneuploidy frequently arises during maternal meiosis due to mechanisms such as classical non-disjunction, premature separation of sister chromatids (PSSC), and reverse segregation (RS). Such meiotic aneuploidies are strongly associated with maternal age, with risk of aneuploid conception increasing exponentially starting around age 35. Though less well understood, recent work has also demonstrated that aneuploidy of mitotic origin is particularly prevalent during the initial post-zygotic cell divisions, potentially permitted by relaxation of cell cycle checkpoints prior to embryonic genome activation. Such mitotic errors, which appear to be independent of maternal or paternal age, generate mosaic embryos possessing both normal and aneuploid cells. Mechanisms of mitotic aneuploidy include anaphase lag and mitotic non-disjunction, but also novel phenomena such as multipolar mitotic division, whereby the diploid genome is partitioned among three or more daughter cells, resulting in massive chromosome loss. Such abnormal mitotic divisions are surprisingly common in cleavage-stage embryos and may largely explain the high observed rates of embryonic mortality (~50%) during preimplantation human development.

In light of these observations, preimplantation genetic testing for aneuploidy (PGT-A) has been devised as an approach to improve IVF outcomes by prioritizing chromosomally normal (i.e. euploid) embryos for transfer based on the inferred genetic constitution of an embryo biopsy. First introduced in the early 1990s, PGT-A has been the subject of long-standing controversy in the IVF field, with some meta-analyses and clinical trials drawing its purported benefits into question. Meanwhile, technical platforms underlying the test have steadily improved over time, with the current standard implementation comprising low coverage whole-genome sequencing of DNA extracted from 5-10 trophectoderm cells of day 5 blastocyst-stage embryos. The improved sensitivity and resolution of sequencing-based PGT-A have placed renewed focus on chromosomal mosaicism as a potential confounding factor for diagnosis and interpretation. While uniform aneuploidies arising from meiotic errors are unambiguously harmful, mosaic aneuploidies of mitotic origin are potentially compatible with healthy live birth. Moreover, low-level mosaic aneuploidy may be more prevalent than previously appreciated, systematically underestimated due to the reliance of PGT-A on biopsies of one or few cells. The ability to distinguish meiotic- and mitotic-origin aneuploidies during preimplantation genetic testing (PGT-A) may thus prove valuable for enhancing IVF outcomes, especially for the many patients with no euploid embryos available for transfer. Yet to date, few analytical methods have explicitly attempted to distinguish these forms of aneuploidy. Notably, trisomies of meiotic origin are expected to produce a unique genetic signature, characterized by the presence of three unique parental haplotypes (two from a single parent) and distinct from the mitotic trisomy signature of only two unique haplotypes chromosome-wide (FIG. 1).

Accordingly, there is a need for additional methods, and related aspects, for distinguishing forms of aneuploidy.

SUMMARY

The present disclosure relates, in certain aspects, to methods, systems, and computer readable media of use in classifying meiotic and mitotic trisomies using low coverage sequencing-based PGT-A data (e.g., where less than $\frac{1}{100}$th of the genome is covered by any sequencing read and where aligned reads rarely overlap). Inspired by the related challenge of imputation, the methods disclosed herein overcome the sparse nature of the data by leveraging haplotype structure from a population reference panel. The methods are tested on simulated data of varying sequencing depths and recombination patterns, evaluating its strengths and limitations under realistic scenarios. At higher coverage, it is demonstrated that the methods distinguish trisomies arising in meiosis I and meiosis II based on haplotype signatures near the centromere. The methods thus reveal new biological insight into the fidelity of meiosis and mitosis, while also holding promise for recovering potentially viable embryos from IVF cycles otherwise deemed unsuccessful. These and other aspects will be apparent upon a complete review of the present disclosure, including the accompanying figures.

In one aspect, the present disclosure provides a method of classifying a chromosome number status of a test subject at least partially using a computer. The method includes selecting, by the computer, sequencing reads obtained from the test subject that comprise nucleic acid variants within defined genomic windows to produce sets of observed test subject nucleic acid variants. The method also includes obtaining, by the computer, joint allele frequencies and/or linkage disequilibrium patterns of corresponding nucleic acid variants observed in a reference subject population to produce sets of reference subject joint allele frequency and/or linkage disequilibrium pattern data. In addition, the method also includes classifying the chromosome number status of the test subject using the sets of observed test subject nucleic acid variants and the sets of reference subject joint allele frequency and/or linkage disequilibrium pattern data.

In another aspect, the present disclosure provides a method of distinguishing between meiotic- and mitotic-origin aneuploidies at least partially using a computer. The method includes selecting, by the computer, within defined genomic windows, reads overlapping informative SNPs that tag common haplotype variation, obtaining, by the computer, joint frequencies of corresponding SNPs from a phased panel of ancestry-matched reference haplotypes, and randomly, by the computer, selecting 2-16 sequencing reads. The method also includes computing, by the computer, probabilities of observed alleles under competing trisomy hypotheses, and comparing, by the computer, the hypotheses by computing a likelihood ratio and estimating a mean and variance by sub-sampling random sets of reads using a bootstrapping approach.

In another aspect, the present disclosure provides a method of distinguishing between meiotic- and mitotic-origin aneuploidies at least partially using a computer. The method includes receiving, by the computer, sequencing reads comprising sequence information from an aneuploid chromosome, and dividing, by the computer, the sequence information from the aneuploid chromosome into a plurality of linkage disequilibrium (LD) blocks or genomic windows (GWs). In some embodiments, the method includes obtaining the aneuploid chromosome from a zygotic cell or an embryonic cell. The method also includes selecting, by the computer, one or more of the sequencing reads corresponding to one or more of the plurality of LD blocks or GWs to produce a set of selected sequencing reads, and determining, by the computer, probabilities of observing the selected sequencing reads under a meiotic-origin model and under a mitotic-origin model to produce a set of probability data. In addition, the method also includes aggregating, by the computer, log-likelihood ratios across the plurality of LD blocks or GWs to produce aggregated log-likelihood ratio using the set of probability data, wherein an aggregated log-likelihood ratio significantly greater than zero indicates that the aneuploid chromosome is a meiotic-origin aneuploidy, and wherein an aggregated log-likelihood ratio significantly less than zero indicates that the aneuploid chromosome is a mitotic-origin aneuploidy, thereby distinguishing between the meiotic- and the mitotic-origin aneuploidies. In these contexts, significance is typically defined, for example, by a 95% confidence interval that does not overlap zero. In some embodiments, this corresponding 95% confidence interval is constructed by taking the 2.5% and 97.5% quantiles of the bootstrap distribution. But note that any confidence level can optionally be chosen depending on desired sensitivity vs. specificity.

In some embodiments, a probability that two sequencing reads are obtained from an identical haplotype under the meiotic-origin model is about ⅓. In some embodiments, a probability that two sequencing reads are obtained from an identical haplotype under the mitotic-origin model is about ⅝. In some embodiments, the sequence information comprises a coverage of between about 0.05× and about 0.5×.

In some embodiments, the aneuploid chromosome comprises a trisomy. In some embodiments, the method includes determining whether an aneuploidy is due to a meiosis I error or a meiosis II error when the aneuploid chromosome is a meiotic-origin aneuploidy. In some embodiments, the method includes determining a significance of the aggregated log-likelihood ratio using at least one statistical procedure (e.g., a weighted jackknife procedure, bootstrapping, or the like).

In some embodiments, the methods further include performing whole genome sequencing of nucleic acids obtained from the test subject to produce the sequencing reads. In some embodiments, the sequencing reads comprise a coverage of less than about 2×, less than about 1×, less than about 0.50×, less than about 0.25×, less than about 0.15×, less than about 0.10×, or less than about 0.05× of a genome of the test subject. In some embodiments, the chromosome number status comprises a state selected from the group consisting of: a monosomy, a monoploidy, a haploidy, a disomy, a diploidy, a trisomy, a triploidy, a tetrasomy, a tetraploidy, a pentasomy, a pentaploidy, and a mosaicisim. In some embodiments, the chromosome number status comprises a meiotic-origin aneuploidy, whereas in other embodiments, the chromosome number status comprises a mitotic-origin aneuploidy. In some embodiments, the methods include determining one or more both parental homologs (BPH) and/or one or more single parental homolog (SPH) signatures for the subject.

In some embodiments, an ancestry of the reference subject population substantially matches an ancestry of the test subject. In some embodiments, the test subject comprises an embryo, a fetus, or a postpartum postnatal subject. In some embodiments, the test subject comprises a preimplantation embryo. In some embodiments, the test subject comprises an in utero embryo or an in utero fetus and wherein the method comprises sequencing nucleic acids obtained from the test subject via a maternal carrier of the test subject to produce the sequencing reads. In some embodiments, the nucleic acid variants comprise single nucleotide variants (SNVs), insertions or deletions (indels), gene fusions, copy number variants (CNVs), transversions, translocations, frame shifts, duplications, epigenetic variants, and repeat expansions.

In some embodiments, the methods include randomly resampling two or more of the sequencing reads in the set of observed test subject nucleic acid variants to produce one or more resampled test subject alleles for each of the defined genomic windows. In some embodiments, the methods include randomly resampling between about 2 and about 1000 of the sequencing reads, between about 3 and about 100 of the sequencing reads, between about 4 and about 50 of the sequencing reads, between about 5 and about 30 of the sequencing reads, or between about 6 and about 20 of the sequencing reads. In some embodiments, the methods include computing likelihood distributions of the resampled test subject alleles under at least two competing chromosome number status hypotheses for each of the defined genomic windows. In some embodiments, the methods include computing the likelihood distributions of the resampled test subject alleles using one or more statistical models. FIG. 8 shows a table with examples of statistical models that can be used when sampling 2, 3, and 4 sequencing reads according to some embodiments of the methods disclosed herein. Additional statistical models that are optionally used are described further herein. In some embodiments, the methods include comparing the competing chromosome number status hypotheses by computing a log likelihood ratio for each of the defined genomic windows. In some embodiments, the methods include estimating a mean value and a variance value by resampling random sets of sequencing reads using at least one bootstrapping approach for each of the defined genomic windows to produce a set of bootstrap distributions. In some embodiments, the methods include combining the log likelihood ratios from multiple defined genomic windows to produce a combined log likelihood ratio. In some embodiments, the methods include estimating a confidence interval using a mean value and a variance value for the combined log likelihood ratio.

In some embodiments, the defined genomic windows are non-overlapping. In some embodiments, the defined genomic windows comprise between about 2 and about 100000 defined genomic windows, between about 3 and about 10000 defined genomic windows, between about 4 and about 1000 defined genomic windows, between about 5 and about 100 defined genomic windows, between about 10 and about 75 defined genomic windows, between about 20 and about 50 defined genomic windows, or between about 30 and about 40 defined genomic windows. In some embodiments, a given defined genomic window comprises a length of between about 5 bases and about 1000000 bases, between about 10 bases and about 100000 bases, between about 100 bases and about 10000 bases, or between about 500 bases and about 1000 bases.

In another aspect, the present disclosure provides a system, comprising at least one controller that comprises, or is capable of accessing, computer readable media comprising non-transitory computer executable instructions which, when executed by at least one electronic processor, perform at least: selecting sequencing reads obtained from the test subject that comprise nucleic acid variants within defined genomic windows to produce sets of observed test subject nucleic acid variants; obtaining joint allele frequencies and/or linkage disequilibrium patterns of corresponding nucleic acid variants observed in a reference subject population to produce sets of reference subject joint allele frequency and/or linkage disequilibrium pattern data; and classifying the chromosome number status of the test subject using the sets of observed test subject nucleic acid variants and the sets of reference subject joint allele frequency and/or linkage disequilibrium pattern data.

In another aspect, the present disclosure provides a system, comprising at least one controller that comprises, or is capable of accessing, computer readable media comprising non-transitory computer executable instructions which, when executed by at least one electronic processor, perform at least: selecting within defined genomic windows, reads overlapping informative SNPs that tag common haplotype variation; obtaining joint frequencies of corresponding SNPs from a phased panel of ancestry-matched reference haplotypes; randomly selecting 2-16 sequencing reads; computing probabilities of observed alleles under competing trisomy hypotheses; and comparing the hypotheses by computing a likelihood ratio and estimating a mean and variance by sub-sampling random sets of reads using a bootstrapping approach.

In another aspect, the present disclosure provides a system, comprising at least one controller that comprises, or is capable of accessing, computer readable media comprising non-transitory computer executable instructions which, when executed by at least one electronic processor, perform at least: receiving sequencing reads comprising sequence information from an aneuploid chromosome; dividing the sequence information from the aneuploid chromosome into a plurality of linkage disequilibrium (LD) blocks or genomic windows (GWs); selecting one or more of the sequencing reads corresponding to one or more of the plurality of LD blocks or GWs to produce a set of selected sequencing reads; determining probabilities of observing the selected sequencing reads under a meiotic-origin model and under a mitotic-origin model to produce a set of probability data; and aggregating log-likelihood ratios across the plurality of LD blocks or GWs to produce aggregated log-likelihood ratio using the set of probability data, wherein an aggregated log-likelihood ratio significantly greater than zero indicates that the aneuploid chromosome is a meiotic-origin aneuploidy, and wherein an aggregated log-likelihood ratio significantly less than zero indicates that the aneuploid chromosome is a mitotic-origin aneuploidy. In these contexts, significance is typically defined, for example, by a 95% confidence interval that does not overlap zero. In some embodiments, this corresponding 95% confidence interval is constructed by taking the 2.5% and 97.5% quantiles of the bootstrap distribution. But note that any confidence level can optionally be chosen depending on desired sensitivity vs. specificity.

In another aspect, the present disclosure provides a computer readable media comprising non-transitory computer executable instructions which, when executed by at least electronic processor, perform at least: selecting sequencing reads obtained from the test subject that comprise nucleic acid variants within defined genomic windows to produce sets of observed test subject nucleic acid variants; obtaining joint allele frequencies and/or linkage disequilibrium patterns of corresponding nucleic acid variants observed in a reference subject population to produce sets of reference subject joint allele frequency and/or linkage disequilibrium pattern data; and classifying the chromosome number status of the test subject using the sets of observed test subject nucleic acid variants and the sets of reference subject joint allele frequency and/or linkage disequilibrium pattern data.

In another aspect, the present disclosure provides a computer readable media comprising non-transitory computer executable instructions which, when executed by at least electronic processor, perform at least: selecting within defined genomic windows, reads overlapping informative SNPs that tag common haplotype variation; obtaining joint frequencies of corresponding SNPs from a phased panel of ancestry-matched reference haplotypes; randomly selecting 2-16 sequencing reads; computing probabilities of observed alleles under competing trisomy hypotheses; and comparing the hypotheses by computing a likelihood ratio and estimating a mean and variance by sub-sampling random sets of reads using a bootstrapping approach.

In another aspect, the present disclosure provides a computer readable media comprising non-transitory computer executable instructions which, when executed by at least electronic processor, perform at least: receiving sequencing reads comprising sequence information from an aneuploid chromosome; dividing the sequence information from the aneuploid chromosome into a plurality of linkage disequilibrium (LD) blocks; selecting one or more of the sequencing reads corresponding to one or more of the plurality of LD blocks or GWs to produce a set of selected sequencing reads; determining probabilities of observing the selected sequencing reads under a meiotic-origin model and under a mitotic-origin model to produce a set of probability data; and aggregating log-likelihood ratios across the plurality of LD blocks or GWs to produce aggregated log-likelihood ratio using the set of probability data, wherein an aggregated log-likelihood ratio significantly greater than zero indicates that the aneuploid chromosome is a meiotic-origin aneuploidy, and wherein an aggregated log-likelihood ratio significantly less than zero indicates that the aneuploid chromosome is a mitotic-origin aneuploidy. In these contexts, significance is typically defined, for example, by a 95% confidence interval that does not overlap zero. In some embodiments, this corresponding 95% confidence interval is constructed by taking the 2.5% and 97.5% quantiles of the bootstrap distribution. But note that any confidence level can optionally be chosen depending on desired sensitivity vs. specificity.

In some embodiments of the system or computer readable media disclosed herein, a probability that two sequencing reads are obtained from an identical haplotype under the meiotic-origin model is about ⅓. In some embodiments of the system or computer readable media disclosed herein, a probability that two sequencing reads are obtained from an identical haplotype under the mitotic-origin model is about ⅝. In some embodiments of the system or computer readable media disclosed herein, the sequence information comprises a coverage of between about 0.05× and about 0.5×. In some embodiments of the system or computer readable media disclosed herein, the instructions further perform determining whether an aneuploidy is due to a meiosis I error or a meiosis II error when the aneuploid chromosome is a meiotic-origin aneuploidy. In some embodiments of the system or computer readable media disclosed herein, the instructions further perform determining a significance of the aggregated log-likelihood ratio using at least one statistical procedure (e.g., a weighted jackknife procedure, bootstrapping, or the like).

In some embodiments of the system or computer readable media disclosed herein, the instructions further perform determining one or more both parental homologs (BPH) and/or one or more single parental homolog (SPH) signatures for the subject. In some embodiments of the system or computer readable media disclosed herein, an ancestry of the reference subject population substantially matches an ancestry of the test subject. In some embodiments of the system or computer readable media disclosed herein, the nucleic acid variants comprise single nucleotide variants (SNVs), insertions or deletions (indels), gene fusions, copy number variants (CNVs), transversions, translocations, frame shifts, duplications, epigenetic variants, and repeat expansions. In some embodiments of the system or computer readable media disclosed herein, the instructions further perform randomly resampling two or more of the sequencing reads in the set of observed test subject nucleic acid variants to produce one or more resampled test subject alleles for each of the defined genomic windows.

In some embodiments of the system or computer readable media disclosed herein, the instructions further perform randomly resampling between about 2 and about 1000 of the sequencing reads, between about 3 and about 100 of the sequencing reads, between about 4 and about 50 of the sequencing reads, between about 5 and about 30 of the sequencing reads, or between about 6 and about 20 of the sequencing reads. In some embodiments of the system or computer readable media disclosed herein, the instructions further perform computing likelihood distributions of the resampled test subject alleles under at least two competing chromosome number status hypotheses for each of the defined genomic windows. In some embodiments of the system or computer readable media disclosed herein, the instructions further perform computing the likelihood distributions of the resampled test subject alleles using one or more statistical models. In some embodiments of the system or computer readable media disclosed herein, the instructions further perform comparing the competing chromosome number status hypotheses by computing a log likelihood ratio for each of the defined genomic windows. In some embodiments of the system or computer readable media disclosed herein, the instructions further perform estimating a mean value and a variance value by resampling random sets of sequencing reads using at least one bootstrapping approach for each of the defined genomic windows to produce a set of bootstrap distributions. In some embodiments of the system or computer readable media disclosed herein, the instructions further perform combining the log likelihood ratios from multiple defined genomic windows to produce a combined log likelihood ratio. In some embodiments of the system or computer readable media disclosed herein, the instructions further perform estimating a confidence interval using a mean value and a variance value for the combined log likelihood ratio.

In some embodiments of the system or computer readable media disclosed herein, the defined genomic windows are non-overlapping. In some embodiments of the system or computer readable media disclosed herein, the defined genomic windows comprise between about 2 and about 100000 defined genomic windows, between about 3 and about 10000 defined genomic windows, between about 4 and about 1000 defined genomic windows, between about 5 and about 100 defined genomic windows, between about 10 and about 75 defined genomic windows, between about 20 and about 50 defined genomic windows, or between about 30 and about 40 defined genomic windows. In some embodiments of the system or computer readable media disclosed herein, a given defined genomic window comprises a length of between about 5 bases and about 1000000 bases, between about 10 bases and about 100000 bases, between about 100 bases and about 10000 bases, or between about 500 bases and about 1000 bases.

In some embodiments of the system or computer readable media disclosed herein, a probability that two sequencing reads are obtained from an identical haplotype under a non-admixed meiotic-origin model is about $\frac{1}{3}$. In some embodiments of the system or computer readable media disclosed herein, a probability that two sequencing reads are obtained from an identical haplotype under a non-admixed mitotic-origin model is about $\frac{5}{9}$. In some embodiments of the system or computer readable media disclosed herein, a probability that two sequencing reads are obtained from an identical haplotype, which is associated with a specific ancestry, under an admixed meiotic-origin model is about $\frac{5}{18}$. In some embodiments of the system or computer readable media disclosed herein, a probability that two sequencing reads are obtained from identical haplotype, which is associated with a specific ancestry, under an admixed mitotic-origin model is about $\frac{1}{6}$.

BRIEF DESCRIPTION OF THE DRAWINGS

The accompanying drawings, which are incorporated in and constitute a part of this specification, illustrate certain embodiments, and together with the written description, serve to explain certain principles of the methods, systems, and related computer readable media disclosed herein. The description provided herein is better understood when read in conjunction with the accompanying drawings which are included by way of example and not by way of limitation. It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

FIGS. 4A-D schematically depict exemplary method steps according to some aspects disclosed herein.

FIG. 8 is a table that shows examples of statistical models for sampling sequencing reads according to some aspects disclosed herein.

FIG. 7 Mapping of meiotic crossovers on putative trisomic chromosomes based on inferred switches between tracts of BPH and SPH trisomy. Samples with less than 0.01× coverage were excluded from the analysis. A. Putative crossovers (vertical lines) observed for trisomic chromosomes of four representative samples. Error bars denote 70% confidence intervals. B. Annotated ideogram of meiotic crossovers detected in each chromosomal bin of all autosomes across the entire sample.

DEFINITIONS

Figure 1:
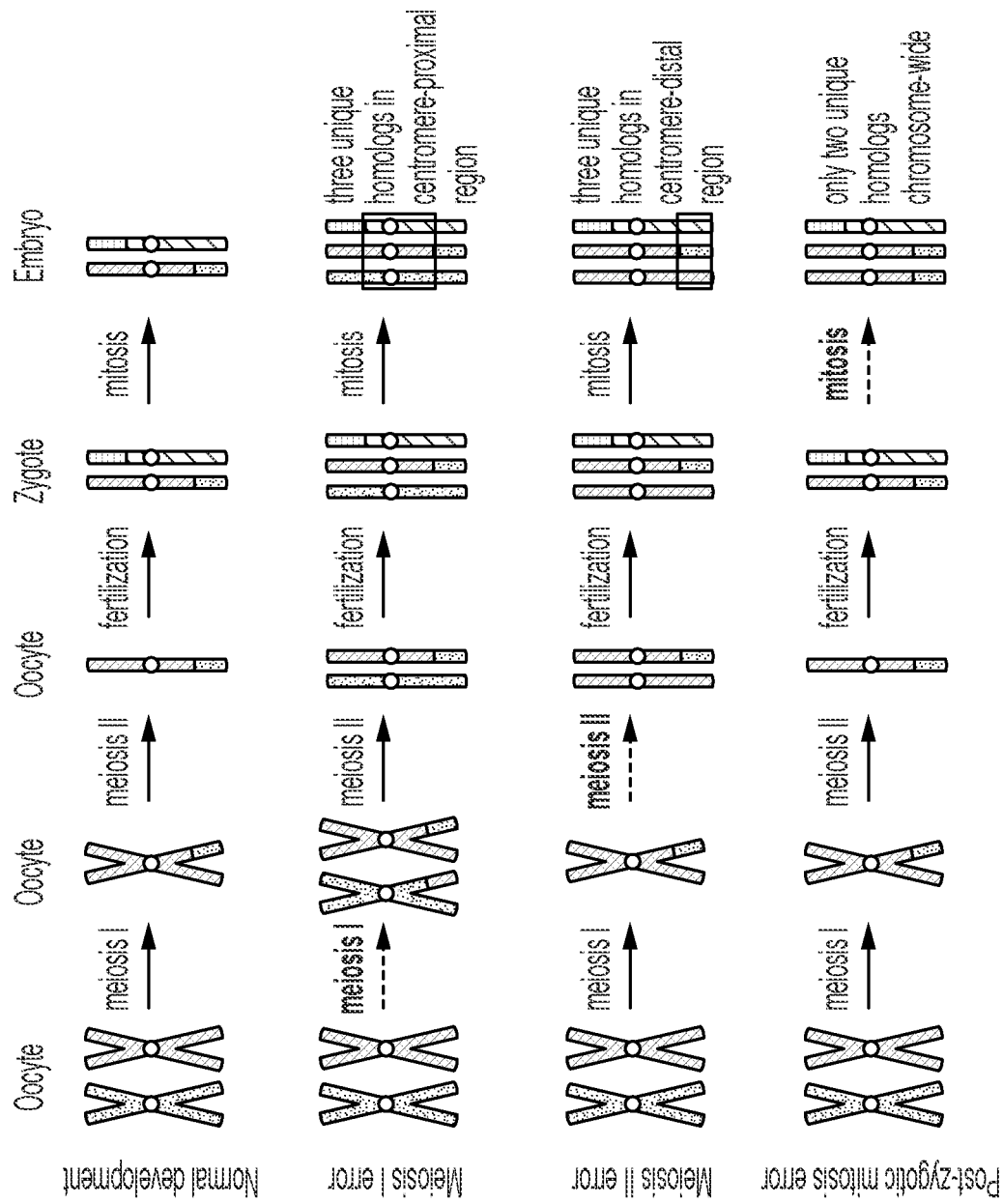
FIG. 1 is a schematic depicting types of meiotic and mitotic errors.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, computer readable media, systems, and component parts, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Allele Frequency. As used herein, "allele frequency" refers to the relative frequency of an allele at a particular locus in a population or in a given subject. Allele frequency is typically expressed as a fraction or percentage.

Coverage: As used herein, "coverage" refers to the number of nucleic acid molecules that represent a particular base position.

Next Generation Sequencing: As used herein, "next generation sequencing" or "NGS" refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

Sequencing: As used herein, "sequencing" refers to any of a number of technologies used to determine the sequence (e.g., the identity and order of monomer units) of a biomolecule, e.g., a nucleic acid such as DNA or RNA. Exemplary sequencing methods include, but are not limited to, targeted sequencing, single molecule real-time sequencing, exon or exome sequencing, intron sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performer by a gene analyzer such as, for example, gene analyzers commercially available from Illumina, Inc., Pacific Biosciences, Inc., or Applied Biosystems/Thermo Fisher Scientific, among many others.

Sequence Information: As used herein, "sequence information" in the context of a nucleic acid polymer means the order and identity of monomer units (e.g., nucleotides, etc.) in that polymer.

Subject: As used herein, "subject" or "test subject" refers to an animal, such as a mammalian species (e.g., human) or avian (e.g., bird) species. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or pathology or a predisposition to the disease or pathology, or an individual that is in need of therapy or suspected of needing therapy. The terms "individual" or "patient" are intended to be interchangeable with "subject." A "reference subject" refers to a subject known to have or lack specific properties (e.g., known ocular or other pathology and/or the like).

DETAILED DESCRIPTION

Extra or missing chromosomes—a phenomenon termed aneuploidy— frequently arises during human meiosis and post-zygotic mitosis and is the leading cause of pregnancy loss, including in the context of in vitro fertilization (IVF). While meiotic aneuploidies affect all cells and are deleterious, mitotic errors generate mosaicism, which may be compatible with healthy live birth. Distinguishing meiotic and mitotic errors may therefore improve the efficacy of preimplantation genetic testing for aneuploidy (PGT-A), which seeks to rank IVF embryos for transfer based on their inferred ploidy statuses. The present disclosure provides in certain aspects a statistical method for distinguishing meiotic and mitotic trisomies based on analysis of low-coverage whole-genome sequencing data, which is the current standard for PGT-A. In some embodiments, the sparse nature of the data is overcome by leveraging allele frequencies and haplotype patterns observed in a phased population reference panel such as the 1000 Genomes Project. In certain embodiments, the methods disclosed herein retain power to distinguish meiotic and mitotic trisomies down to coverage as low as about 0.05× and at higher coverage can also distinguish between meiosis I and meiosis II errors based on centromere-proximal signatures. We further assess robustness of the model to mismatches between the ancestries of the target sample and the reference panel and present an approach to mitigate this concern. Together, the methods and related aspects of the present disclosure provide fundamental insight into the mechanistic origins of trisomies during human development, as well as a practical tool for improving embryo selection during IVF, among other applications.

Figure 9:
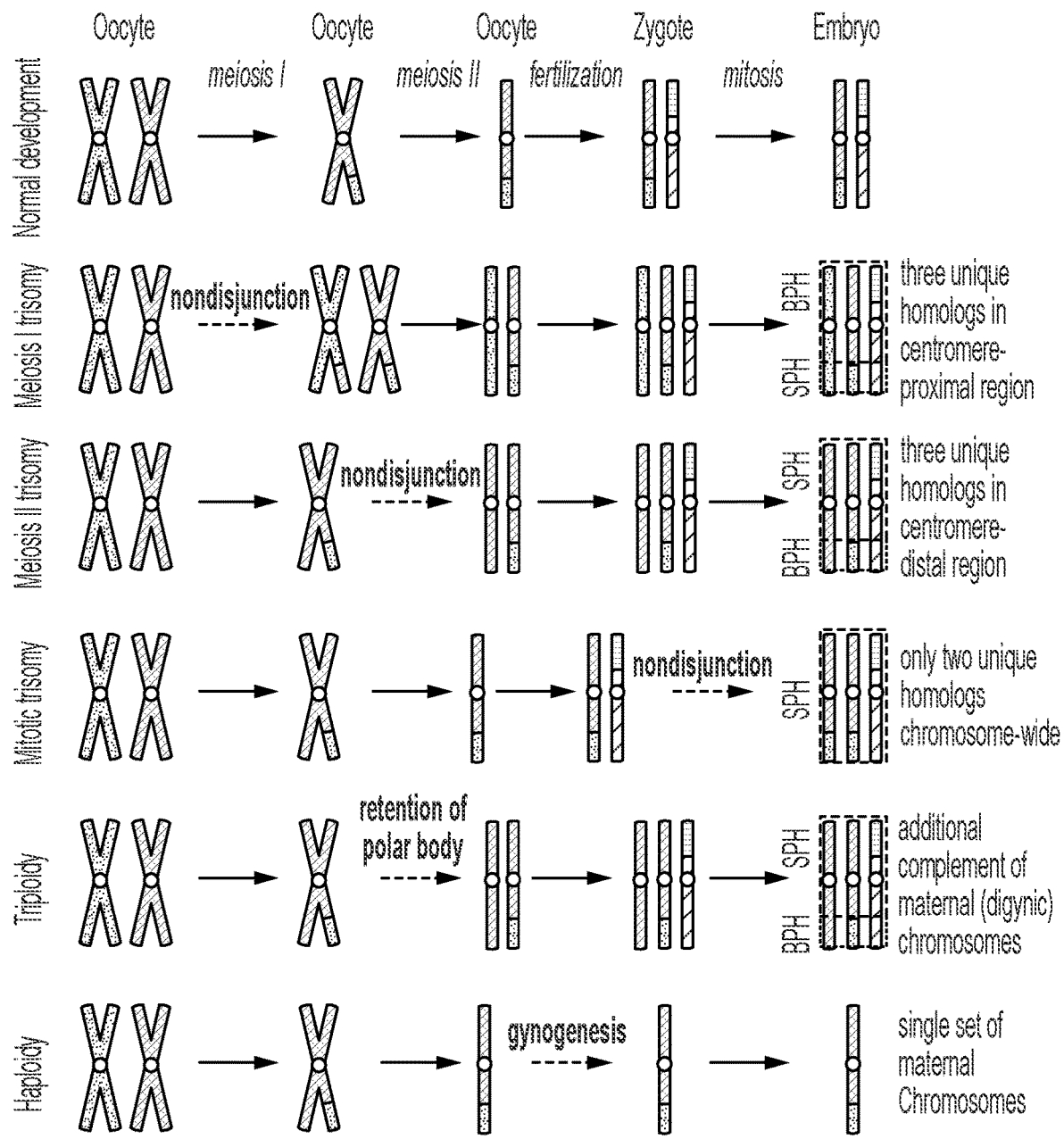
FIG. 9 schematically shows signatures of various forms of chromosome abnormality with respect to their composition of identical and distinct parental homologs. Normal gametogenesis produces two genetically distinct copies of each chromosome—one copy from each parent—that comprise mosaics of two homologs possessed by each parent. Meiotic-origin trisomies may be diagnosed by the presence of one or more tracts with three distinct parental homologs (i.e., transmission of both parental homologs [BPH] from a given parent). In contrast, mitotic-origin trisomies are expected to exhibit only two genetically distinct parental homologs chromosome-wide (i.e. duplication of a single parental homolog [SPH] from a given parent). Triploidy and haploidy will mirror patterns observed for individual meiotic trisomies and monosomies, respectively, but across all 23 chromosome pairs—a pattern that confounds standard coverage-based analysis of PGT-A data.

In some exemplary embodiments, meiotic and mitotic trisomies (aneuploidies involving three copies of a chromosome) are discerned based on the unique signatures that they leave within the genotype data. For example, the harmful aneuploidies that arise via meiosis typically generate signatures of three genetically distinct chromosome copies (denoted as "BPH"; FIG. 9). In contrast, the potentially viable mitotic trisomies harbor a signature of only two distinct chromosome copies (2 of the three copies are identical; denoted as "SPH"; FIG. 9). In some embodiments, the sparse nature of the data is overcome by taking advantage of the fact that patterns of genetic variation are correlated in the population. Thus, even sparse observations permit probabilistic inferences of genotypes in unobserved parts of the genome. In some of these embodiments, this is accomplished through the use of statistical models (FIG. 10) that describe the probabilities of particular genotype observations, given the patterns of genetic variation observed in a population reference panel (e.g., using publicly available data such as the 1000 Genomes Project or the like). In some of these embodiments, the likelihoods of the data under the meiotic trisomy and mitotic trisomy hypothesis are then contrasted. Typically, the statistical models are generic (e.g., any number of chromosomes involving any combination of identical or distinct homologs can be accommodated), and naturally extend to the related problem of detecting aneuploidies that involve all copies of a chromosome (such as, for example, triploidy or haploidy), which are typically missed by previous methods. FIG. 8 shows a table with examples of statistical models that can be used when sampling 2, 3, and 4 sequencing reads according to some embodiments of the methods disclosed herein. Optionally, essentially any number of sequencing reads can be accommodated by these methods.

The methods disclosed herein also work for subjects of admixed ancestry (e.g., subjects or individuals with recent ancestors from different continental super-populations such as European and East Asian), which accounts for a large proportion of the population. These and other aspects will be apparent upon a complete review of the present disclosure including the accompanying figures.

Figure 2:
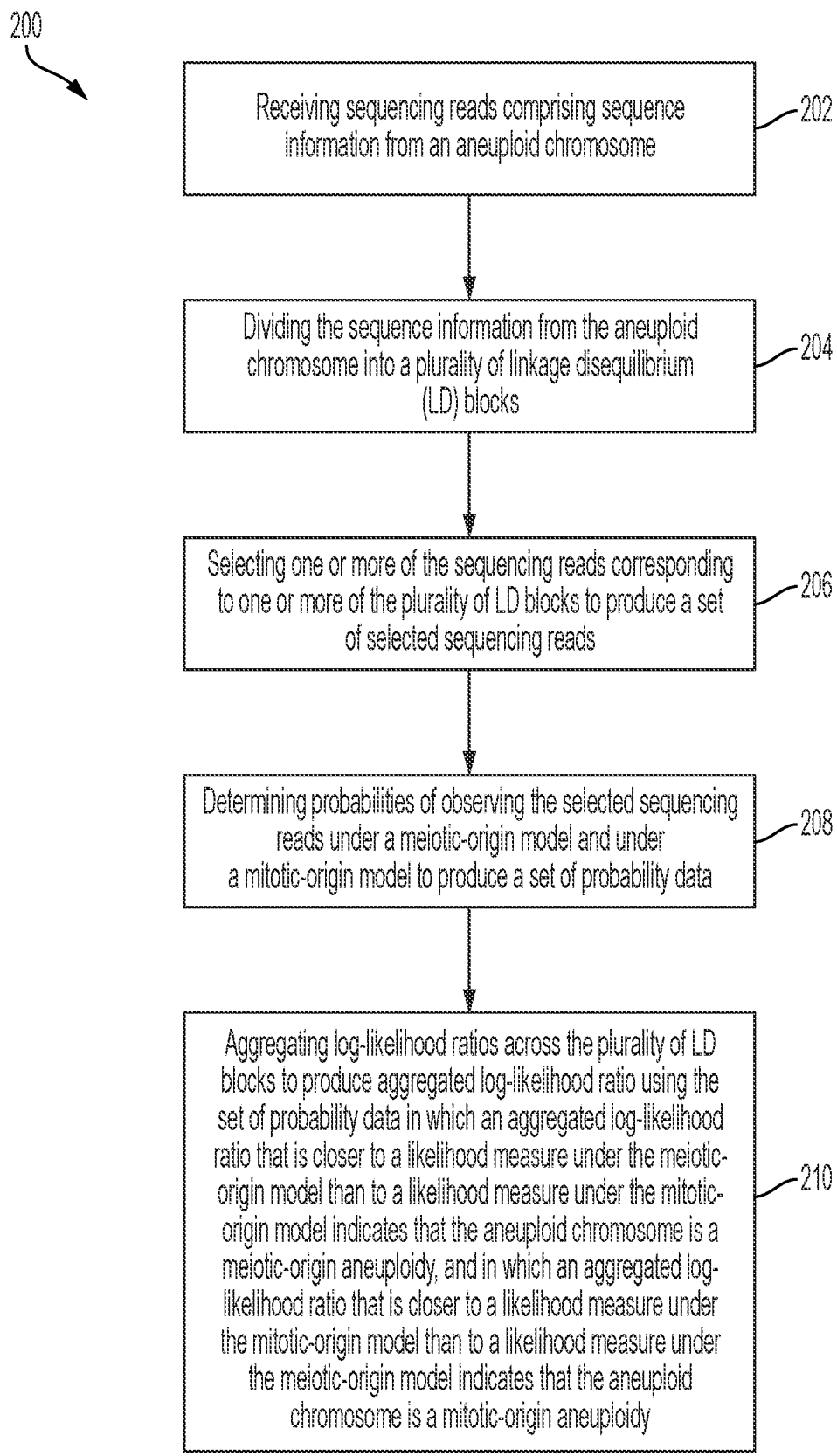
FIG. 2 is a flow chart that schematically depicts exemplary method steps according to some aspects disclosed herein.

To illustrate, FIG. 2 is a flow chart that schematically depicts exemplary method steps of distinguishing between meiotic- and mitotic-origin aneuploidies at least partially using a computer. As shown, method 200 includes receiving, by the computer, sequencing reads comprising sequence information from an aneuploid chromosome (step 202), and dividing, by the computer, the sequence information from the aneuploid chromosome into a plurality of linkage disequilibrium (LD) blocks (step 204). In some embodiments, method 200 includes obtaining the aneuploid chromosome from a zygotic cell or an embryonic cell. Method 200 also includes selecting, by the computer, one or more of the sequencing reads corresponding to one or more of the plurality of LD blocks or GWs to produce a set of selected sequencing reads (step 206), and determining, by the computer, probabilities of observing the selected sequencing reads under a meiotic-origin model and under a mitotic-origin model to produce a set of probability data (step 208). In addition, method 200 also includes aggregating, by the computer, log-likelihood ratios across the plurality of LD blocks or GWs to produce aggregated log-likelihood ratio using the set of probability data in which an aggregated log-likelihood ratio significantly greater than zero indicates that the aneuploid chromosome is a meiotic-origin aneuploidy, and wherein an aggregated log-likelihood ratio significantly less than zero indicates that the aneuploid chromosome is a mitotic-origin aneuploidy (step 210). In these contexts, significance is typically defined, for example, by a 95% confidence interval that does not overlap zero. In some embodiments, this corresponding 95% confidence interval is constructed by taking the 2.5% and 97.5% quantiles of the bootstrap distribution. But note that any confidence level can optionally be chosen depending on desired sensitivity vs. specificity.

In some embodiments, a probability that two sequencing reads are obtained from an identical haplotype under the meiotic-origin model is about $\frac{1}{3}$. In some embodiments, a probability that two sequencing reads are obtained from an identical haplotype under the mitotic-origin model is about $\frac{5}{9}$. In some embodiments, the sequence information comprises a coverage of between about 0.05× and about 0.5×.

In some embodiments, the aneuploid chromosome comprises a trisomy. In some embodiments, the method includes determining whether an aneuploidy is due to a meiosis I error or a meiosis II error when the aneuploid chromosome is a meiotic-origin aneuploidy. In some embodiments, the method includes determining a significance of the aggregated log-likelihood ratio using at least one statistical procedure (e.g., a weighted jackknife procedure or the like).

To further illustrate, FIG. 4 schematically depicts exemplary method steps of distinguishing between meiotic- and mitotic-origin aneuploidies. As shown, the method includes, within defined genomic windows, select reads overlapping informative SNPs that tag common haplotype variation (panel A). The method also includes obtaining joint frequencies of corresponding SNPs from a phased panel of ancestry-matched reference haplotypes (panel B). The method also includes randomly selecting 2-16 reads and computing probabilities of observed alleles under competing trisomy hypotheses (panel C). In addition, the method also includes comparing the hypotheses by computing a likelihood ratio and estimating the mean and variance by sub-sampling random sets of reads using a bootstrapping approach (panel D).

Figure 6:
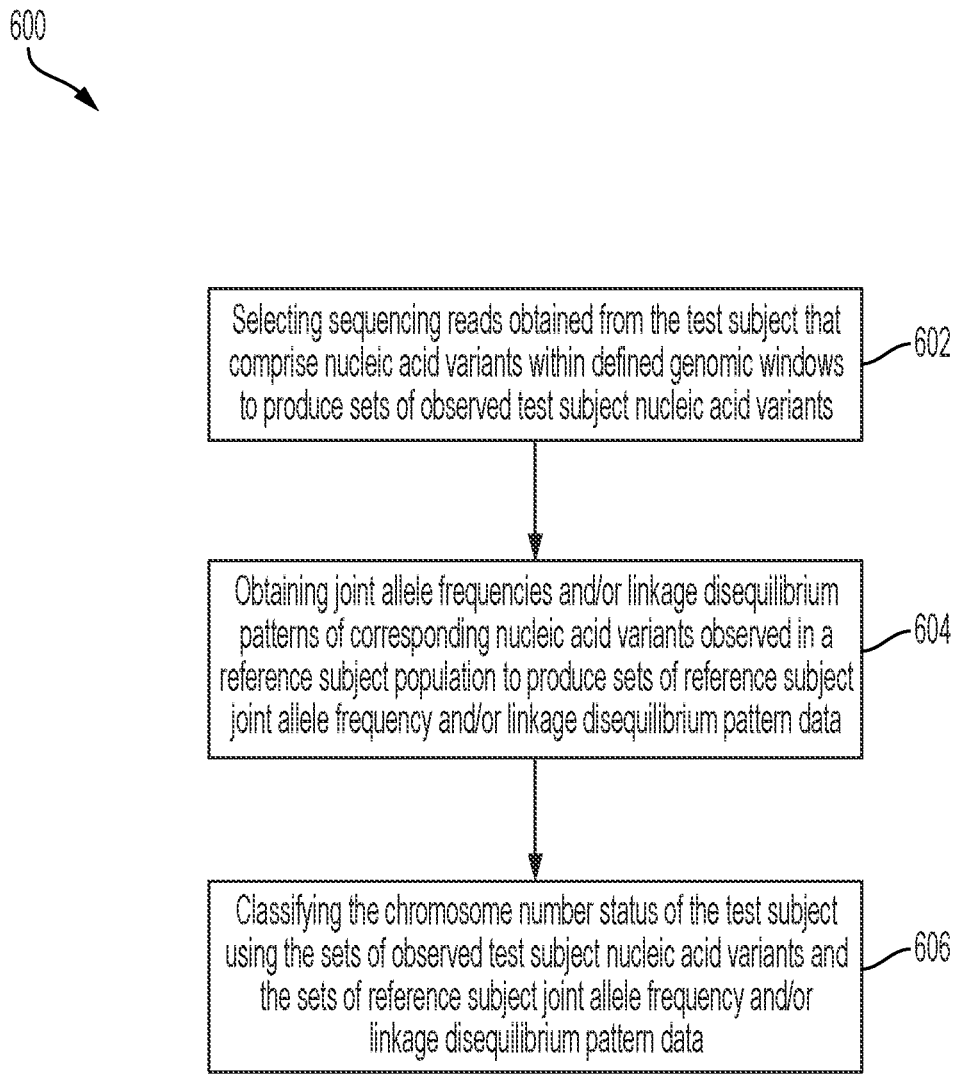
FIG. 6 is a flow chart that schematically depicts exemplary method steps according to some aspects disclosed herein.
Figure 7:
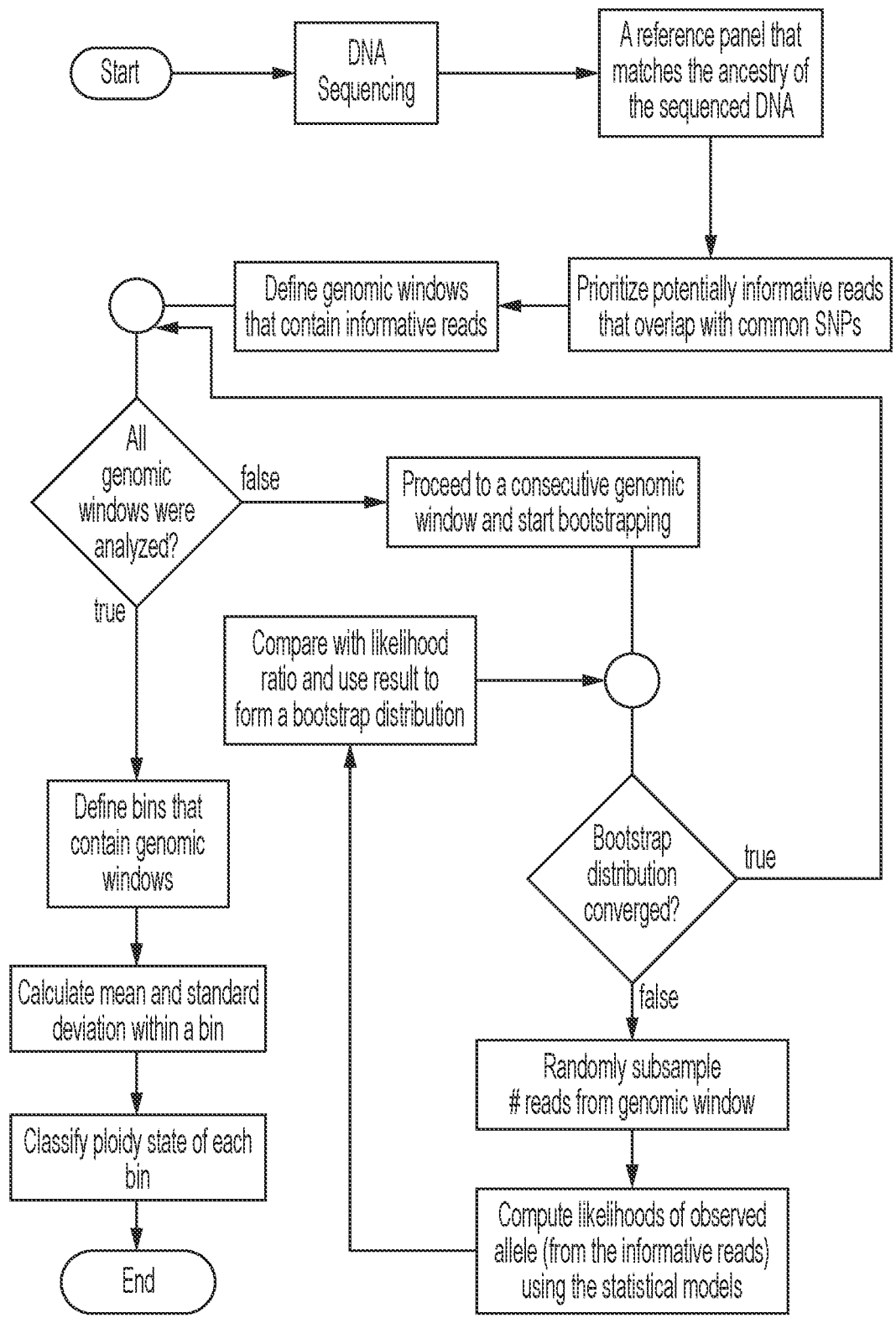
FIG. 7 is a flow chart that schematically depicts an exemplary algorithm according to some aspects disclosed herein.

To further illustrate, FIG. 6 is a flow chart that schematically depicts exemplary method steps of classifying a chromosome number status of a test subject, typically at least partially using a computer. As shown, method 600 includes selecting sequencing reads obtained from the test subject that comprise nucleic acid variants within defined genomic windows to produce sets of observed test subject nucleic acid variants (step 602). Method 600 also includes obtaining joint allele frequencies and/or linkage disequilibrium patterns of corresponding nucleic acid variants observed in a reference subject population to produce sets of reference subject joint allele frequency and/or linkage disequilibrium pattern data (step 604). In addition, method 600 also includes classifying the chromosome number status of the test subject using the sets of observed test subject nucleic acid variants and the sets of reference subject joint allele frequency and/or linkage disequilibrium pattern data (step 606). As a further exemplary illustration, FIG. 7 is a flow chart that schematically depicts an algorithm that is used according to some aspects disclosed herein.

In some embodiments, the methods disclosed herein further include performing whole genome sequencing of nucleic acids obtained from the test subject to produce the sequencing reads. In some embodiments, the sequencing reads comprise a coverage of less than about 2×, less than about 1×, less than about 0.50×, less than about 0.25×, less than about 0.15×, less than about 0.10×, or less than about 0.05× of a genome of the test subject. In some embodiments, the chromosome number status comprises a state selected from the group consisting of: a monosomy, a monoploidy, a haploidy, a disomy, a diploidy, a trisomy, a triploidy, a tetrasomy, a tetraploidy, a pentasomy, a pentaploidy, and a mosaicisim. In some embodiments, the chromosome number status comprises a meiotic-origin aneuploidy, whereas in other embodiments, the chromosome number status comprises a mitotic-origin aneuploidy. In some embodiments, the methods include determining one or more both parental homologs (BPH) and/or one or more single parental homolog (SPH) signatures for the subject.

In some embodiments, an ancestry of the reference subject population substantially matches an ancestry of the test subject. In some embodiments, the test subject comprises an embryo, a fetus, or a postpartum postnatal subject. In some embodiments, the test subject comprises a preimplantation embryo. In some embodiments, the test subject comprises an in utero embryo or an in utero fetus and wherein the method comprises sequencing nucleic acids obtained from the test subject via a maternal carrier of the test subject to produce the sequencing reads. In some embodiments, the nucleic acid variants comprise single nucleotide variants (SNVs), insertions or deletions (indels), gene fusions, copy number variants (CNVs), transversions, translocations, frame shifts, duplications, epigenetic variants, and repeat expansions.

In some embodiments, the methods include randomly resampling two or more of the sequencing reads in the set of observed test subject nucleic acid variants to produce one or more resampled test subject alleles for each of the defined genomic windows. In some embodiments, the methods include randomly resampling between about 2 and about 1000 of the sequencing reads, between about 3 and about 100 of the sequencing reads, between about 4 and about 50 of the sequencing reads, between about 5 and about 30 of the sequencing reads, or between about 6 and about 20 of the sequencing reads. In some embodiments, the methods include computing likelihood distributions of the resampled test subject alleles under at least two competing chromosome number status hypotheses for each of the defined genomic windows. In some embodiments, the methods include computing the likelihood distributions of the resampled test subject alleles using one or more statistical models. In some embodiments, the methods include comparing the competing chromosome number status hypotheses by computing a log likelihood ratio for each of the defined genomic windows. In some embodiments, the methods include estimating a mean value and a variance value by resampling random sets of sequencing reads using at least one bootstrapping approach for each of the defined genomic windows to produce a set of bootstrap distributions. In some embodiments, the methods include combining the log likelihood ratios from multiple defined genomic windows to produce a combined log likelihood ratio. In some embodiments, the methods include estimating a confidence interval using a mean value and a variance value for the combined log likelihood ratio.

In some embodiments, the defined genomic windows are non-overlapping. In some embodiments, the defined genomic windows comprise between about 2 and about 100000 defined genomic windows, between about 3 and about 10000 defined genomic windows, between about 4 and about 1000 defined genomic windows, between about 5 and about 100 defined genomic windows, between about 10 and about 75 defined genomic windows, between about 20 and about 50 defined genomic windows, or between about 30 and about 40 defined genomic windows. In some embodiments, a given defined genomic window comprises a length of between about 5 bases and about 1000000 bases, between about 10 bases and about 100000 bases, between about 100 bases and about 10000 bases, or between about 500 bases and about 1000 bases.

Figure 3:
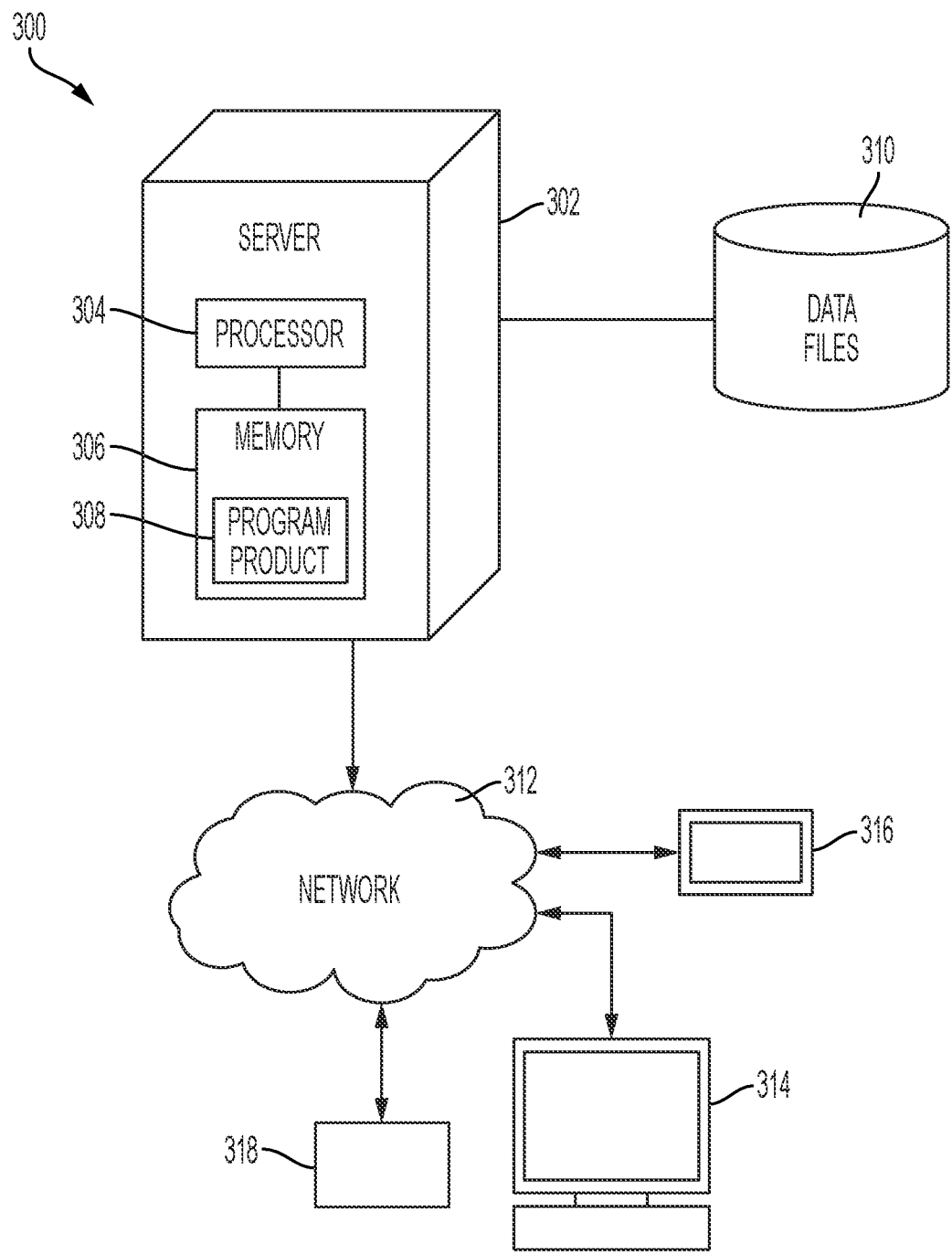
FIG. 3 is a schematic diagram of an exemplary system suitable for use with certain aspects disclosed herein.
Figure 5:
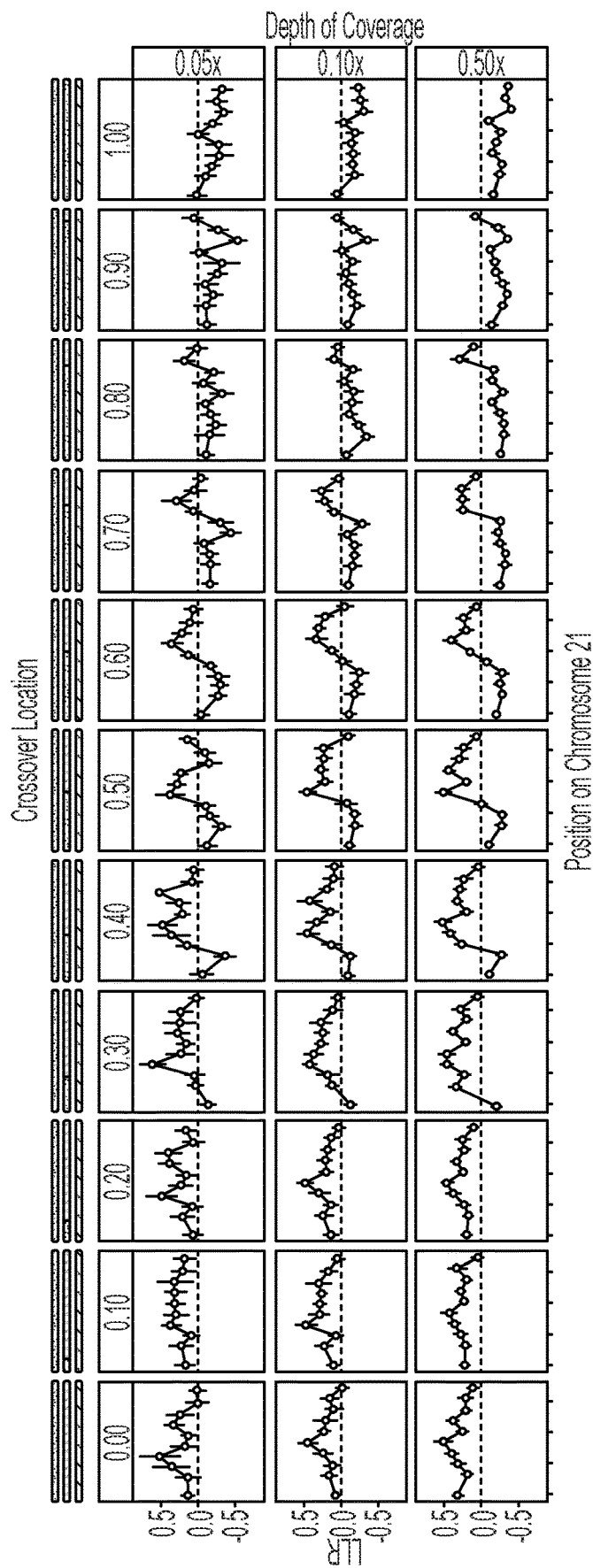
FIG. 5 are plots showing classification results upon applying an embodiment of the methods disclosed herein to trisomy simulations with varying depths of coverage and meiotic crossover locations. The simulation focuses on Chromosome 21 due to its status as the shortest human chromosome, thus providing a conservative view of model performance.

The present disclosure also provides various systems and computer program products or machine readable media. In some aspects, for example, the methods described herein are optionally performed or facilitated at least in part using systems, distributed computing hardware and applications (e.g., cloud computing services), electronic communication networks, communication interfaces, computer program products, machine readable media, electronic storage media, software (e.g., machine-executable code or logic instructions) and/or the like. To illustrate, FIG. 3 provides a schematic diagram of an exemplary system suitable for use with implementing at least aspects of the methods disclosed in this application. As shown, system 300 includes at least one controller or computer, e.g., server 302 (e.g., a search engine server), which includes processor 304 and memory, storage device, or memory component 306, and one or more other communication devices 314, 316, (e.g., client-side computer terminals, telephones, tablets, laptops, other mobile devices, etc. (e.g., for receiving captured images and/or videos for further analysis, etc.)) positioned remote from camera device 318, and in communication with the remote server 302, through electronic communication network 312, such as the Internet or other internetwork. Communication devices 314, 316 typically include an electronic display (e.g., an internet enabled computer or the like) in communication with, e.g., server 302 computer over network 312 in which the electronic display comprises a user interface (e.g., a graphical user interface (GUI), a web-based user interface, and/or the like) for displaying results upon implementing the methods described herein. In certain aspects, communication networks also encompass the physical transfer of data from one location to another, for example, using a hard drive, thumb drive, or other data storage mechanism. System 300 also includes program product 308 (e.g., related to implementing a method of distinguishing between meiotic- and mitotic-origin aneuploidies as described herein) stored on a computer or machine readable medium, such as, for example, one or more of various types of memory, such as memory 306 of server 302, that is readable by the server 302, to facilitate, for example, a guided search application or other executable by one or more other communication devices, such as 314 (schematically shown as a desktop or personal computer). In some aspects, system 300 optionally also includes at least one database server, such as, for example, server 310 associated with an online website having data stored thereon (e.g., entries corresponding to more reference panels, etc.) searchable either directly or through search engine server 302. System 300 optionally also includes one or more other servers positioned remotely from server 302, each of which are optionally associated with one or more database servers 310 located remotely or located local to each of the other servers. The other servers can beneficially provide service to geographically remote users and enhance geographically distributed operations.

As understood by those of ordinary skill in the art, memory 306 of the server 302 optionally includes volatile and/or nonvolatile memory including, for example, RAM, ROM, and magnetic or optical disks, among others. It is also understood by those of ordinary skill in the art that although illustrated as a single server, the illustrated configuration of server 302 is given only by way of example and that other types of servers or computers configured according to various other methodologies or architectures can also be used. Server 302 shown schematically in FIG. 3, represents a server or server cluster or server farm and is not limited to any individual physical server. The server site may be deployed as a server farm or server cluster managed by a server hosting provider. The number of servers and their architecture and configuration may be increased based on usage, demand and capacity requirements for the system 300. As also understood by those of ordinary skill in the art, other user communication devices 314, 316 in these aspects, for example, can be a laptop, desktop, tablet, personal digital assistant (PDA), cell phone, server, or other types of computers. As known and understood by those of ordinary skill in the art, network 312 can include an internet, intranet, a telecommunication network, an extranet, or world wide web of a plurality of computers/servers in communication with one or more other computers through a communication network, and/or portions of a local or other area network.

As further understood by those of ordinary skill in the art, exemplary program product or machine readable medium 308 is optionally in the form of microcode, programs, cloud computing format, routines, and/or symbolic languages that provide one or more sets of ordered operations that control the functioning of the hardware and direct its operation. Program product 308, according to an exemplary aspect, also need not reside in its entirety in volatile memory, but can be selectively loaded, as necessary, according to various methodologies as known and understood by those of ordinary skill in the art.

As further understood by those of ordinary skill in the art, the term "computer-readable medium" or "machine-readable medium" refers to any medium that participates in providing instructions to a processor for execution. To illustrate, the term "computer-readable medium" or "machine-readable medium" encompasses distribution media, cloud computing formats, intermediate storage media, execution memory of a computer, and any other medium or device capable of storing program product 508 implementing the functionality or processes of various aspects of the present disclosure, for example, for reading by a computer. A "computer-readable medium" or "machine-readable medium" may take many forms, including but not limited to, non-volatile media, volatile media, and transmission media. Non-volatile media includes, for example, optical or magnetic disks. Volatile media includes dynamic memory, such as the main memory of a given system. Transmission media includes coaxial cables, copper wire and fiber optics, including the wires that comprise a bus. Transmission media can also take the form of acoustic or light waves, such as those generated during radio wave and infrared data communications, among others. Exemplary forms of computer-readable media include a floppy disk, a flexible disk, hard disk, magnetic tape, a flash drive, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave, or any other medium from which a computer can read.

Program product 308 is optionally copied from the computer-readable medium to a hard disk or a similar intermediate storage medium. When program product 308, or portions thereof, are to be run, it is optionally loaded from their distribution medium, their intermediate storage medium, or the like into the execution memory of one or more computers, configuring the computer(s) to act in accordance with the functionality or method of various aspects. All such operations are well known to those of ordinary skill in the art of, for example, computer systems.

To further illustrate, in certain aspects, this application provides systems that include one or more processors, and one or more memory components in communication with the processor. The memory component typically includes one or more instructions that, when executed, cause the processor to provide information that causes sequence information, related data, and/or the like to be displayed (e.g., upon being received from nucleic acid sequencing device 318 and/or via communication devices 314, 316 or the like) and/or receive information from other system components and/or from a system user (e.g., via nucleic acid sequencing device 318 and/or via communication devices 314, 316, or the like).

In some aspects, program product 308 includes non-transitory computer-executable instructions which, when executed by electronic processor 304 perform at least: selecting within defined genomic windows, reads overlapping informative SNPs that tag common haplotype variation; obtaining joint frequencies of corresponding SNPs from a phased panel of ancestry-matched reference haplotypes; randomly selecting 2-16 sequencing reads; computing probabilities of observed alleles under competing trisomy hypotheses; and comparing the hypotheses by computing a likelihood ratio and estimating a mean and variance by sub-sampling random sets of reads using a bootstrapping approach. Other exemplary executable instructions that are optionally performed are described further herein.

Additional details relating to computer systems and networks, databases, and computer program products are also provided in, for example, Peterson, *Computer Networks: A Systems Approach*, Morgan Kaufmann, 5th Ed. (2011), Kurose, *Computer Networking: A Top-Down Approach*, Pearson, $7^{th}$ Ed. (2016), Elmasri, *Fundamentals of Database Systems*, Addison Wesley, 6th Ed. (2010), Coronel, *Database Systems: Design, Implementation, & Management*, Cengage Learning, $11^{th}$ Ed. (2014), Tucker, *Programming Languages*, McGraw-Hill Science/Engineering/Math, 2nd Ed. (2006), and Rhoton, *Cloud Computing Architected: Solution Design Handbook*, Recursive Press (2011), which are each incorporated by reference in their entirety.

EXAMPLE 1: CLASSIFYING THE ORIGINS OF ANEUPLOIDY TO IMPROVE EMBRYO SELECTION WITH PREIMPLANTATION GENETIC TESTING

Results

A Statistical Model to Distinguish Between Meiotic- and Mitotic-Origin Trisomies One consequence of linkage disequilibrium (LD) in a population is that observing an allele at one locus in the genome informs the probability of observing other alleles at loci on the same haplotype. Our approach leverages LD to determine whether two sequencing reads originated from the same chromosome, based on known patterns of linkage between alleles observed on those reads. This approach allows us to determine whether a PGT-A sample contains three unique copies of a chromosome (i.e., BPH), a sign of meiotic aneuploidy.

Consider an embryo trisomic for a chromosome. There are two hypotheses that can explain this trisomy: First, it may have occurred through meiotic error, resulting in an embryo containing two distinct homologs from one parent and a third distinct homolog from the other parent (BPH; FIG. 1). Second, the trisomy may have occurred during mitotic divisions in the developing embryo, resulting in an embryo with two identical copies of one parental homolog and a second distinct homolog from the other parent (SPH). Although the SPH case does not allow us to distinguish mitotic errors from a rare meiotic error without recombination between the two homologs from the same parent (FIG. 1), the BPH case is an unambiguous signature of deleterious meiotic aneuploidy.

Our statistical model is based on the premise that the probability of drawing two reads from the same haplotype differs under the BPH and SPH scenarios. If a pair of reads originates from identical homologs, the probability of observing the alleles on these reads is given by the joint probability of the linked alleles. If a pair of reads originates from two different homologs, the probability of observing their associated alleles is simply equal to the product of the allele frequencies, since these alleles are unlinked. Because BPH and SPH result in different ratios of identical and distinct homologs, they create differences in how often we expect to see reads from the same homolog (⅓ and ⅝, respectively; FIG. 1).

Distinguishing these scenarios in low-coverage data (0.05-0.5×) is challenging due to the fact that reads rarely overlap one another at sites that would distinguish the different homologs. Our model thus leverages patterns of LD from large population reference panels, using an approach related to imputation. Specifically, the length of the trisomic chromosome is divided into LD blocks of size $10^4$-$10^5$ bp. For each LD block, several reads are selected, and the probabilities of observing the contained alleles are calculated under the two models. The probabilities are compared as a log-likelihood ratio (LLR), the LLRs are aggregated across all LD blocks, and a weighted jackknife procedure is used to assess significance.

We define a log likelihood score as the log of the likelihood under the meiotic trisomy hypothesis minus the log of the likelihood under the mitotic trisomy hypothesis. Likelihoods refer to the probability of the data under each respective model.

Consider SNP loci in physical proximity on the same chromosome in LD; A pair of haplotypes that partly overlap with these SNP positions were observed from two independent shotgun reads. We compare the likelihoods of the observed haplotypes under two competing hypotheses.

Selecting a Population Genetic Reference Panel of Human Haplotypes

We estimated the probability of observing two given alleles on the same haplotype by using a reference panel of phased genotypes from the 1000 Genomes Phase 3 dataset. Specifically, a set of individuals of matched ancestry to the target sample were extracted from the 1000 Genomes Project samples to construct a phased reference panel. Notably, any phased genomic dataset of matched ancestry could be used in place of the 1000 Genomes Project dataset, with performance maximized in large datasets with closely matched ancestry.

Such estimates have the virtue that they do not depend on theoretical assumptions, but simply on the sample's having been randomly drawn from the genetically similar populations. A drawback, which we take into account, is that reliable estimations of probabilities that are either very close to zero, or very close to one use large reference panels. In practice, it is sufficient to construct the reference panels using statistically phased genotypes from surveys of human genetic diversity, such as the 1000 Genomes Project.

DISCUSSION

Performance of the method degrades below approximately 0.05× coverage, which is a function of the amount of genetic variation that exists in human genomes (mean pairwise nucleotide difference ($\pi$)≈0.01).

The methods typically assumes uniform trisomy within the biopsy (i.e. all trisomic cells). If the biopsy itself is mosaic, that can be detected, albeit with some error, by current NGS-based methods of PGT-A and classified as likely mitotic. Our method complements such an approach, effectively adding to the pool of putative mitotic aneuploidies by recovering them from those that would typically be presumed as meiotic in origin.

The ability to reliably distinguish viable forms of mosaic aneuploidy from harmful meiotic aneuploidy offers new hope to many patients by recovering healthy embryos from IVF cycles otherwise deemed unsuccessful.

APPENDIX

Prioritizing Informative Reads

We developed a scoring algorithm to prioritize reads based on their potential information content, as determined by measuring haplotype diversity within a reference panel at sites that overlap each read.

We emphasize that the priority score of a read only depends on variation within the reference panel and not on the alleles that the read contains.

The score of a read is calculated as follows:
Based on our reference panel, we list all the biallelic SNPs that overlap with the read and their reference and alternative alleles.
Using the former list, we list all the possible haplotypes. In a region that contain n biallelic SNPs there are $2^n$ possible haplotypes.
The frequency of each haplotype is estimated from the reference panel by computing the joint frequency of the alleles that comprise each haplotype.
We increment the priority score of a read by one for every haplotype with a frequency between $f_0$ and $1-f_0$.
The scoring metric is based on the following principles:
Reads that overlap with potentially informative SNPs with high rates of heterozygosity should receive higher priority. In turn, a high rate of heterozygosity increases the accuracy of the likelihood ratio test. In the simplest case, where a read overlaps with only a single SNP, the score of the read would be two when the minor allele frequency (MAF) is at least $f_0$ and otherwise zero.
All observed alleles from the same read are considered as originating from the same underlying molecule. Thus, the score should reflect the number of informative haplotypes existing in the population at the chromosomal region that overlaps with the read. For a reference panel on the scale of the 1000 Genomes Project (approximately 2500) individuals, 25% 5\% of common SNPs have a nearest neighbor within 35 bp. Hence, even for short reads, the score metric should account for reads that span multiple SNPs.

Likelihood Ratio

Two loci are in linkage disequilibrium (LD) when their alleles are non-randomly associated. One of the main causes of LD is that alleles with physical proximity are often co-inherited. This nonrandom association implies that there is a statistical dependence between the allelic state of one locus and the state of the other.

Our approach is based on the idea that observations of a set of alleles from one read consistently provide information about the allelic states in another read that originated from the same DNA fragment via LD. On the other hand, when comparing haplotypes from two different copies of a chromosome, each haplotype provides no predictive information about alleles within the other haplotype.

Consider SNP loci in physical proximity on the same chromosome in LD; A pair of haplotypes that partly overlap with these SNP positions were observed from two independent shotgun reads. We compare the likelihood of the observed haplotypes under two competing hypotheses:

The presence of three unmatched homologous chromosomes, denoted as BPH (both parental homologs).

The presence of two identical homologs with a third unmatched homolog, denoted as SPH (single parental homolog).

Our statistical models are based on the premise that for the two trisomy scenarios the odds of two reads being drawn from the same haplotypes differ. While for three unmatched homologs the odds are 1:2, for two matched homologs out of three the odds are 5:4. In the case that a pair of reads were drawn from matched homologs, the probability of observing the two haplotypes is given by the joint probability of these two haplotypes. In contrast, if a pair or reads were drawn from unmatched homologs then the probability of observing the two haplotypes is simply the product of the two haplotype frequencies in the population.

$$P_{BPH}(A \wedge B) = \frac{1}{3}f(AB) + \frac{2}{3}f(A)f(B). \quad (1)$$

$$P_{SPH}(A \wedge B) = \frac{5}{9}f(AB) + \frac{4}{9}f(A)f(B). \quad (2)$$

These two probabilities are compared as a log likelihood ratio, which is calculated as:

$$\gamma(A, B) = \log \frac{P_1(A \wedge \wedge B)}{P_2(1 \wedge B)}$$

To estimate empirically these probabilities, we count the occurrences of single haplotypes as well as pairs of haplotypes in a reference panel of phased genotypes. Such estimates have the virtue that they do not depend on theoretical assumptions, but simply on the sample's having been randomly drawn from the genetically similar populations. A drawback, which we take into account, is that reliable estimations of probabilities that are either very close to zero, or very close to one requires large reference panels. In practice, it is sufficient to construct the reference panels using statistically phased genotypes from surveys of human genetic diversity, such as the 1000 Genome Project.

Bootstrapping

The ranking algorithm ranks each read according to the number of different haplotypes that the reference panel supports at the chromosomal region that overlaps with the read.

In each LD block, between 2 to 16 reads with a rank larger than one are randomly selected from a uniform distribution. Then, the probabilities of observed alleles under competing trisomy hypotheses are calculated and the hypotheses are compared using a log-likelihood ratio test (LLR) test.

The sample mean and the unbiased sample variance (i.e. with Bessel's correction) of the LLR in each LD block are calculated by repeating this process in a bootstrapping approach.

Since one in three most-common SNP positions occur on average in a human diploid, subsampling 16 short reads that overlap with these most common SNP positions is sufficient. When the number of reads in a LD block is less than 16, the number of subsampled reads is smaller by one than the total number of reads.

Since the number of terms in the statistical models grow exponentially, we subsample at most 16 reads. Moreover, estimating accurately the joint frequency of a large number of alleles requires a very large reference panel.

Coarse-Graining Strategy for Tracking Recombination

Recombination rate in humans is 1.6 Cm/Mb, that is, for every $10^6$ base pairs there is a 1.6 in a 100 chance of crossover on average per generation.

Clustering dozens of LD blocks (the size of a LD block is $\approx 10^5$ allows detecting accurately the recombination events by averaging the LLR over the LD blocks in each cluster.

In extremely low coverages, where the standard error of the cluster mean LLR cannot be calculated via the Bienayme formula (because resampling of some LD block is not possible), the weight Jackknife technique is used for estimation.

Determining Optimal LD Block Size

In order to ensure the effectiveness of the subsampling, each LD block should contain at least n+1 reads, where n is the number of reads in each subsample.

We define one LD block after another, adjusting its size to include at least 1.5×n reads.

The size of each LD block varies between $5 \times 10^4$ bp to $30 \times 10^4$ by in steps of $10^4$ bp.

Creating a Multi-Ethnic Reference Panel

In the case that ancestry is unknown, it may be preferable to select a reference panel that is insensitive to mismatches with the ancestry of the target sample. Here we describe one approach to this end:

We identify the SNPs that exist across the five superpopulations, i.e. African, Ad Mixed Americans, East Asian, European and South Asian.

The LD between these common SNPs is calculated for each superpopulation, where the LD between the alleles A and B is defined by $D_{AB}=f(AB)/(f(A)f(B))$.

The LD between neighbor SNPs is compared across the five superpopulations to identify a set SNPs with ancestry independent linkage.

Only SNPs that their minor allele count in each superpopulation is at least one are considered.

For each superpopulation, a LD matrix is created; The elements of the spase matrix are $D_{AB}$ if the distance between the alleles A and B does not exceed $10^5$ bp, and zero otherwise.

The LD matrix is a block matrix that includes the LD between both reference and alternative alleles with neighbor reference and alternative alleles.

For each pair of superpopulations, matching elements of LD matrices are compared. Then, a table of all the SNPs vs. the fraction of LDs that do not share the same magnitude is created.

The SNPs with the m largest fractions are removed from the LD matrices and a new table is created.

The former step is repeated until all the elements in one LD matrix have the same magnitude as their corresponding elements in the second LD matrix.

This process is done between each pair of superpopulations and in the end a list of all the stable SNPs is created.

Simulating Meiotic- and Mitotic-Origin Trisomies

The final phase of the 1000 Genomes Project (phase 3) contains fully phased haplotypes for 2,504 individuals. The genotypes were extracted from VCF files to effectively form a set of haploid sequences.

For each simulated trisomy, three haploid sequences were chosen based on their attributed superpopulation. In addition, the chromosome number to be simulated is chosen together with k crossover points.

Our simulations focus on chromosome 21, the smallest human chromosome that is likely to accommodate only a single recombination event. For simplicity, we assume a singular event, resulting a switch from a SPH to a BPH scenario.

We pick a random position in chromosome 21 from a uniform distribution. Chromosome positions that are left to crossover point fall in the SPH region and the rest in BPH region.

Then, one out of three 21 chromosomes is drawn from a weighted distribution. The weighted distribution depends on the chromosome position that was picked. In the BPH region all the three chromosomes have the same weight, making it effectively a uniform distribution. In the SPH region the first chromosome has twice the weight of the second chromosome, while the third chromosome has no weight.

From the drawn chromosome, a segment of length/that starts at the picked chromosomal position is added to simulated sequence data, to mimic a read from a sequencing platform.

The process of adding segments, from a random chromosome and a random chromosomal position, to the simulated sequence data is repeated until the required depth of coverage is obtained.

Generalization of the Method to Arbitrary Ploidy Hypotheses

Let us consider m reads from a numbered chromosome with a copy number of n, containing/unique homologs. We list all the possibilities to assign the reads among the different homologs. For example, in the case of two reads, denoted by A and 8, and two unique homologs the list contains four configuration, i.e., ({A}, {B}), ({B}, {A}), ({AB}, )(, {AB})

To each configuration in the list we assign a weight. The weight depends on the degeneracy of each homologs, e.g., having twice the same homolog means that the degeneracy of this homolog is two.

For each configuration, we list the number of reads that were assigned to each homolog against the degeneracy of these homologs. Moreover, the $i^{th}$ element in the list is $(r_i, d_i)$ where $r_i$ is the number of reads assigned to the $i^{th}$ homolog and $d_i$ is the degeneracy of this homolog. We also note that for each configuration the relations $\Sigma_{i=1}^l r_i = m$ and $\Sigma_{i=1}^l d_i = n$ hold. Then, the weight associated with a configuration is $P_i(d_i)^{r_i}$. • All the configurations that share the same partitioning of reads, regardless to which homolog the subset was assigned, are grouped together. For example, in the case of two reads and two unique homologs there are two possible partitions, i.e., {{A}, {B}} and {{AB}, }.

We associate each partition of reads with the total weight of all the configurations that share the same partition. In the case of two reads from a chromosome with two unique homologs out of three, we have (AB,5) and (A|B,4).

Each partition together with its associated weight, contributed a term to the statistical model. The term is a product of a normalized weight and joint frequencies. The normalization factor is mm and each joint frequency corresponds to a subset of reads, e.g., using the partitions list from the former example we get $$P(AB) = \frac{5}{9} f(AB) + \frac{4}{9} f(A) f(B).$$

An Efficient Way to Encode the Statistical Models

In order to identify common multiples in the statistical model, we group partitions of reads according to their subset with the smallest cardinality.

The partitioning of reads can be encoded efficiently using the occupation basis. In this representation all the reads are enumerated. Each subset of reads is represented by a binary sequence, where the $i^{th}$ element is one when the $i^{th}$ read is included in the subset and zero otherwise. In other words, bits in a binary sequence map to whether a read is included in the subset.

Accounting for the Rate of Heterozygosity

When a read overlaps with a common SNP and the embryo is homozygous at this locus, the assumptions of both the SPH and BPH hypotheses are violated; The likelihood ratio test accounts for the rate of heterozygosity in several ways:

The minimal number of reads that should be subsampled to get a reliable for likelihood ratio test is determined by the rate of heterozygosity, e.g. for a rate of half the minimal number of reads should be four.

The concept of heterozygosity can be generalized to refer to haplotypes instead of alleles. Hence, when any of the alleles that form a haplotype are heterozygous, the entire haplotype is considered heterozygous. All the alleles that were observed on the same read form a haplotype. Since the heterozygosity rate of a haplotype is larger than the rate of an allele, we apply the statistical models on haplotypes.

We use a scoring algorithm to prioritize reads that overlap with highly diverse haplotypes within the a reference panel, as described previously.

TABLE 1

(Top) Table weights for 3 reads under the SPH scenario.
(Bottom) Based on the table a statistical model was derived.

| Haploid 1 (no degeneracy) | Haploid 2 (degeneracy of 2) | Weight | Partition | Total Weight |
|---|---|---|---|---|
| A | BC | $1^1 \times 2^2 = 4$ | A\|BC | 6 |
| BC | A | $1^2 \times 2^1 = 2$ | | |
| B | AC | 4 | B\|AC | 6 |
| AC | B | 2 | | |
| C | AB | 4 | C\|AB | 6 |
| AB | C | 2 | | |
| — | ABC | $1^0 \times 2^3 = 8$ | ABC | 9 |
| ABC | — | $1^3 \times 2^0 = 1$ | | |
| | | | | 27 |

$$P_{SPH}(ABC) = \frac{6}{27}(f(A)f(BC) + f(B)f(AC) + f(C)f(AB)) + \frac{9}{27}f(ABC)$$

EXAMPLE 2: HAPLOTYPE-AWARE INFERENCE OF HUMAN CHROMOSOME ABNORMALITIES

BACKGROUND

Whole-chromosome gains and losses (aneuploidies) are extremely common in human embryos, and are the leading causes of pregnancy loss and congenital disorders, both in the context of in vitro fertilization (IVF) and natural conception. Aneuploidy frequently arises during maternal meiosis due to mechanisms such as classical non-disjunction, premature separation of sister chromatids, and reverse segregation. Such meiotic aneuploidies are strongly associated with maternal age, with risk of aneuploid conception increasing exponentially starting around age 35. Though less well understood, research has also demonstrated that aneuploidy of mitotic origin is prevalent during the initial post-zygotic cell divisions, potentially owing to relaxation of cell cycle checkpoints prior to embryonic genome activation. Such mitotic errors, which are independent of maternal or paternal age, generate mosaic embryos possessing both normal and aneuploid cells. Mechanisms of mitotic aneuploidy include anaphase lag and mitotic non-disjunction, but also newly appreciated phenomena such as multipolar mitotic division. Such abnormal mitoses are surprisingly common in cleavage-stage embryos and partially explain the high observed rates of embryonic mortality (~50%) during preimplantation human development.

In light of these observations, preimplantation genetic testing for aneuploidy (PGT-A) has been developed as an approach to improve IVF outcomes by prioritizing chromosomally normal (i.e., euploid) embryos for transfer, based on the inferred genetic constitution of an embryo biopsy. First introduced in the early 1990s, PGT-A has been the subject of long-standing controversy, with some meta-analyses and clinical trials drawing its benefits into question. Meanwhile, technical platforms underlying the test have steadily improved over time, with the current state of the art comprising low-coverage whole-genome sequencing of DNA extracted from 5-10 trophectoderm cells of day-5 blastocyst-stage embryos. The improved sensitivity and resolution of sequencing-based PGT-A have placed a renewed focus on chromosomal mosaicism as a potential confounding factor for diagnosis and interpretation. While uniform aneuploidies arising from meiotic errors are unambiguously harmful, mosaic aneuploidies are potentially compatible with healthy live birth. Moreover, low-level mosaic aneuploidies may be prevalent but systematically underestimated due to the reliance of PGT-A on biopsies of one or few cells.

Another underappreciated challenge in the analysis of sequencing-based PGT-A data is the detection of complex abnormalities including errors in genome-wide ploidy (e.g. triploidy and haploidy). Because existing algorithms detect chromosome abnormalities by comparing the normalized counts of aligned sequencing reads (i.e., depth of coverage) across chromosomes within a sample, inferences are compromised when many or all chromosomes are affected. Extreme cases such as haploidy and triploidy may evade detection entirely and be falsely interpreted as normal euploid samples. Such classification errors are particularly concerning given the association of ploidy abnormalities with molar pregnancy and miscarriage. Triploidy in particular comprises more than 10% of cytogenetically abnormal miscarriages.

The ability to reliably distinguish meiotic- and mitotic-origin aneuploidies, as well as complex and genome-wide errors of ploidy, may thus prove valuable for enhancing IVF outcomes. Notably, trisomy (and triploidy) of meiotic origin is expected to exhibit a unique genetic signature, characterized by the presence of three distinct parental haplotypes (i.e., "both parental homologs" [BPH] from a single parent) in contrast with the mitotic trisomy signature of only two distinct haplotypes chromosome-wide (i.e., "single parental homolog" [SPH] from each parent; FIG. 9). Conversely, monosomy and haploidy will exhibit genetic signatures of only a single haplotype chromosome- or genome-wide, respectively. To date, few methods have explicitly attempted to use these signatures to distinguish these forms of aneuploidy. Exceptions include single nucleotide polymorphism (SNP) microarray based approaches, which require genetic material from both parents, as well as embryo biopsies and targeted sequencing approaches, which require alternative methods of library preparation to sequence short amplicons to higher coverage.

Here we describe a statistical approach to classify aneuploidies using genotype information encoded in low-coverage whole-genome sequencing data from PGT-A. Inspired by the related challenge of imputation, our method overcomes the sparse nature of the data by leveraging information from a population reference panel. We test our method on simulated and empirical data of varying sequencing depths, meiotic recombination patterns, and patient ancestries, evaluating its strengths and limitations under realistic scenarios. At higher coverage, we further demonstrate that our method permits the mapping of meiotic crossovers on trisomic chromosomes, as well as the distinction of trisomies originating in meiosis I and meiosis II. Our method reveals new biological insight into the fidelity of meiosis and mitosis, while also holding promise for improving preimplantation genetic testing.

RESULTS

Genotypic Signatures of Meiotic and Mitotic Aneuploidy

Most contemporary implementations of PGT-A are based on low-coverage (<0.05×) whole-genome sequencing of 5-10 trophectoderm cells biopsied from blastocyst-stage embryos at day 5 or 6 post-fertilization. Given the level of coverage and the paucity of heterozygous sites within human genomes, standard approaches for analyzing such data typically ignore genotype information and instead infer aneuploidies based on deviations in relative coverage across chromosomes within a sample. Inspired by genotype imputation and related forensic methods, we hypothesized that even low-coverage data could provide orthogonal evidence of chromosome abnormalities, complementing and refining the inferences obtained from coverage-based methods. As in imputation, the information content of the genotype data is greater than first appears by virtue of linkage disequilibrium (LD)—the population genetic correlation of alleles at two or more loci in genomic proximity, which together comprise a haplotype. We developed an approach to quantify the probability that two sequencing reads originated from the same chromosome, based on known patterns of LD among alleles observed on those reads. Hereafter, we refer to our method as LD-informed PGT-A (LD-PGTA).

Specifically, in the case of trisomy, we sought to identify a signature of meiotic error wherein portions of the trisomic chromosome are composed of two distinct homologs from one parent and a third distinct homolog from the other parent (BPH; FIG. 9). In contrast, trisomies arising via post-zygotic mitotic errors are composed of two identical copies of one parental homolog and a second distinct homolog from the other parent (SPH). Although this chromosome-wide SPH signature may also capture rare meiotic errors with no recombination (FIG. 9), BPH serves as an unambiguous signature of deleterious meiotic aneuploidy. In the presence of recombination, meiotic trisomies will comprise a mixture of BPH and SPH tracts. BPH tracts that span the centromere are consistent with mis-segregation of homologous chromosomes during meiosis I, while BPH tracts that lie distal to the centromere are consistent with mis-segregation of sister chromatids during meiosis II.

LD-PGTA: a Statistical Model to Classify Aneuploidies

Distinguishing these scenarios in low-coverage data (i1×) is challenging due to the fact that reads rarely overlap one another at sites that would distinguish the different homologs. Our classifier therefore uses patterns of allele frequencies and LD from large population reference panels to account for potential relationships among the sparse reads. Specifically, the length of the trisomic chromosome is divided into genomic windows, on a scale consistent with the length of typical human haplotypes (104-105 bp). For each genomic window, several reads are sampled, and the probabilities of the observed alleles under the BPH trisomy and SPH trisomy hypotheses (i.e., likelihoods) are computed.

Our likelihood functions are based on the premise that the probability of drawing reads from the same haplo-type differs under different ploidy hypotheses, which are defined by various configurations of genetically distinct or identical homologs (FIG. 9). If a pair of reads originates from two identical homologs, the probability of observing the alleles on these reads is given by the joint frequency of the linked alleles. On the other hand, if a pair of reads originates from two different homologs, the probability of observing their associated alleles is simply equal to the product of the allele frequencies, since the alleles are unlinked. Because the BPH and SPH hypotheses are defined by different ratios of identical and distinct homologs, the probability of sampling reads from the same homolog also differs under each hypothesis ($1/3$ and $5/8$, respectively; FIG. 9).

Allele frequencies and joint allele frequencies (i.e., haplotype frequencies) are in turn estimated through examination of a phased population genetic reference panel, ideally matched to the ancestry of the target sample. Such estimates have the virtue that they do not depend on theoretical assumptions, but simply on the sample's having been randomly drawn from the genetically similar populations. A drawback, which we take into account, is that reliable estimates of the frequencies of rare alleles or haplotypes require large reference panels. In practice, it is sufficient to construct the reference panels using statistically phased genotypes from large surveys of human genetic diversity, such as the 1000 Genomes Project (n=2504 individuals).

Given the importance of admixture in contemporary populations, we also generalized our models to allow for scenarios where the maternal and paternal haplotypes derive from distinct ancestral populations (see Methods). These admixture-aware models only require knowledge of the ancestry of the target sample (i.e. embryo), which has an important practical advantage for PGT-A where parental genotype data is typically unavailable.

Figure 10F:
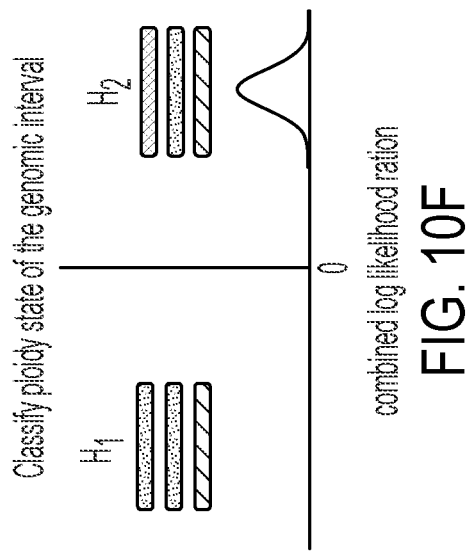
FIG. 10 (Panels A-F) schematically show exemplary method steps for classifying a ploidy state according to some aspects disclosed herein. A. Within defined genomic windows, select reads overlapping informative SNPs that tag common haplotype variation. B. Obtain joint frequencies of corresponding SNPs from a phased panel of ancestry-matched reference haplotypes. C. Randomly resample 2-18 reads and compute probabilities of observed alleles under two competing ploidy hypotheses. D. Compare the hypotheses by computing a likelihood ratio and estimate the mean and variance by re-sampling random sets of reads using a bootstrapping approach. E. Repeat steps A-D for consecutive non-overlapping genomic windows and aggregate the log likelihood ratios over larger genomic intervals. F. Use the mean and variance of the combined log likelihood ratio to estimate a confidence interval and classify the ploidy state of the genomic interval.
Figure 10E:
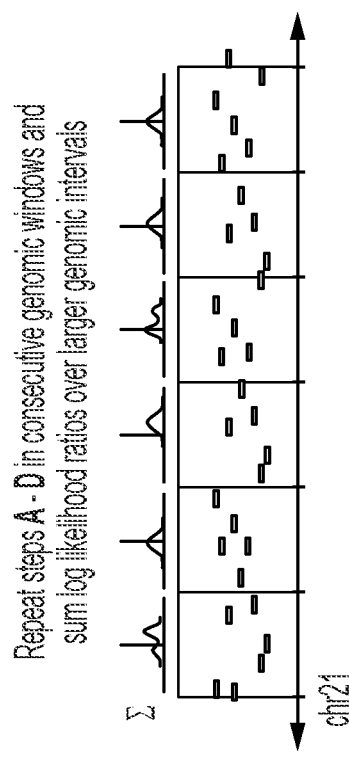
Figure 11:
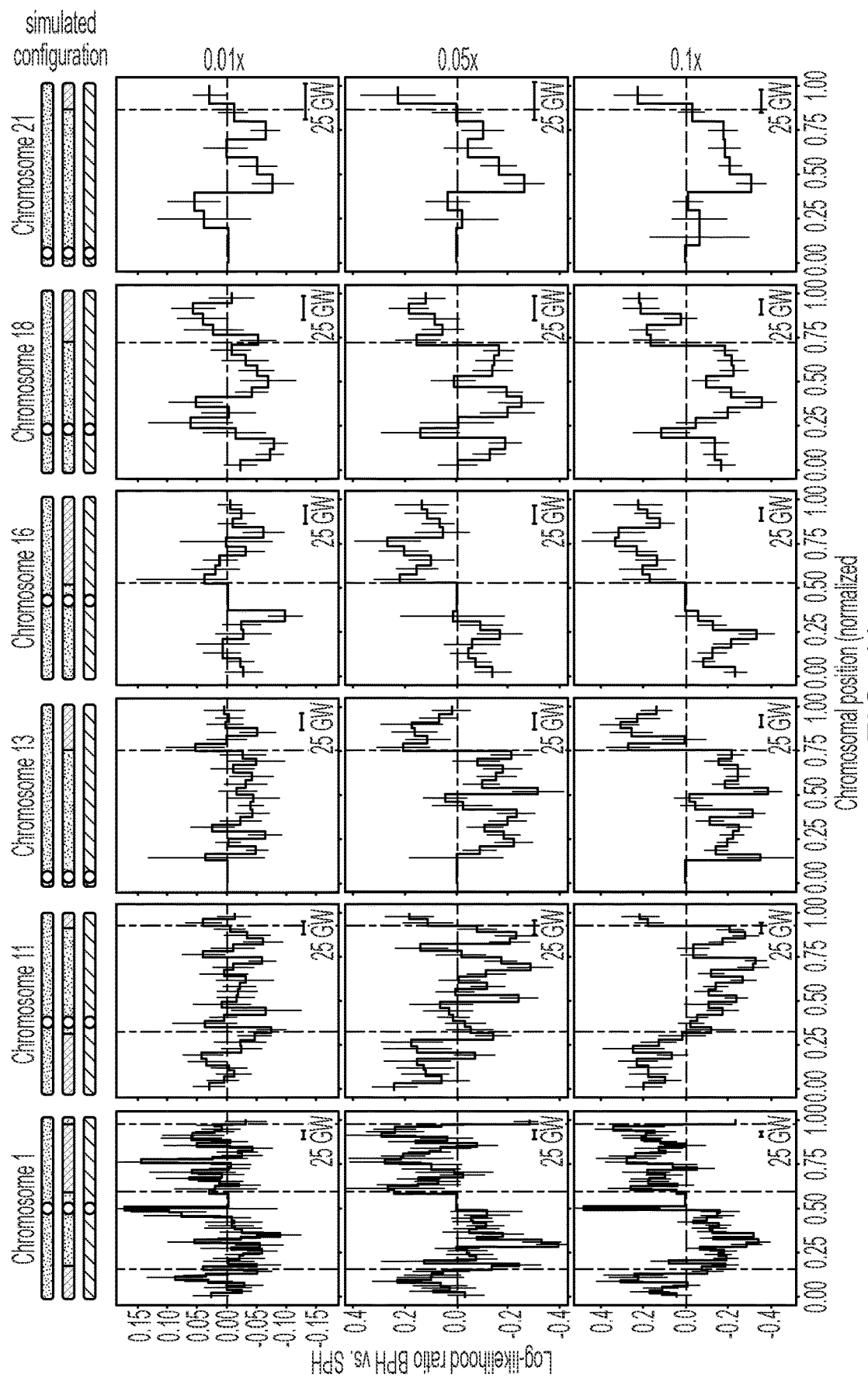
FIG. 11 are plots that demonstrate the detection of meiotic crossovers from low-coverage PGT-A data. Trisomies were simulated with varying locations of meiotic crossovers, as depicted in the upper diagrams and varying depths of coverage (0.01×, 0.05×, and 0.1×). The simulation focused on Chromosome 21 due to its status as the shortest human chromosome, thus providing a conservative view of model performance.

Within each genomic window, we compare the likelihoods under the BPH and SPH hypotheses by computing a log-likelihood ratio (LLR) and use the m out of n bootstrap procedure to assess uncertainty (see Methods; FIG. 10). LLRs are then aggregated across consecutive genomic windows comprising larger intervals (i.e., "bins"). The mean and variance of the combined LLR is used to compute a confidence interval for each bin, which can then be classified as supporting the BPH or SPH hypothesis, depending on whether the bounds of the confidence interval are positive or negative, respectively. Confidence intervals that span zero remain inconclusive, and are classified as "ambiguous".

Benchmarking LD-PGTA With Simulated Sequences

To evaluate our method, we simulated sequencing reads from BPH and SPH trisomies according to their defining haplotype configurations (FIG. 9). Our simulations assumed uniform depth of coverage, random mating (by randomly drawing haplotypes from the 1000 Genomes Project), and equal probability of drawing a read from any of the homologs. We varied the mean depths of coverage (0.01×, 0.05×, and 0.1×) and read lengths (36-250 bp), testing model assumptions and performance over a range of plausible scenarios.

Figure 12A:
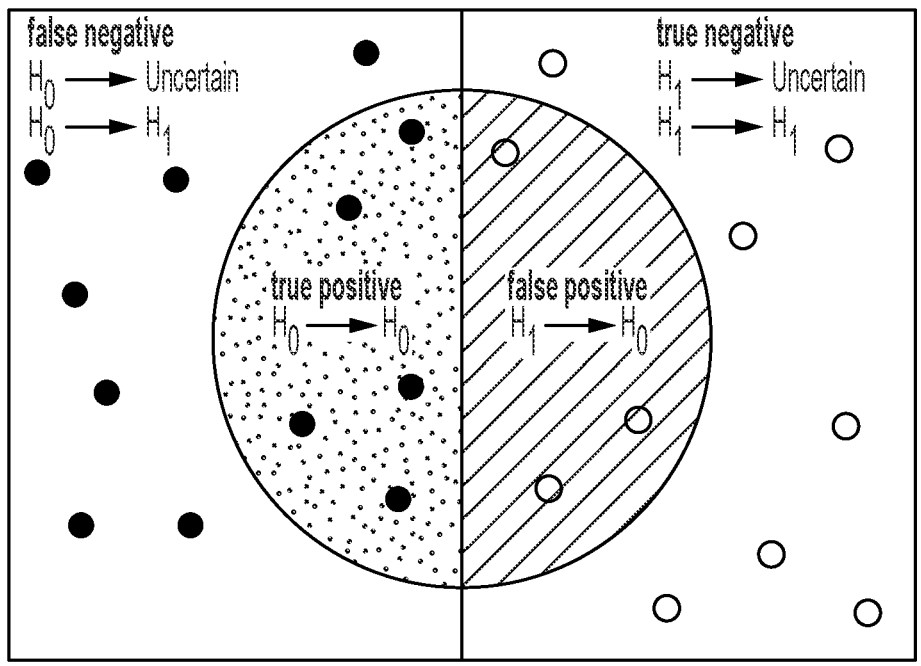
FIG. 12 (Panels A-D). The upper left (right) diagram depicts relative trade-offs between instances classified correctly as $H_0$ ($H_1$) and instances misclassified as $H_0$ ($H_1$). All instances of actual class X that were classified as instances of predicated class Y are denoted by X→Y. The balanced true (false) positive rate is defined as an average of the true (false) positives rates from both diagrams. (A and B). C. Balanced ROC curves for BPH vs. SPH with matched and random reference panels of non-admixed embryos, varying depths of coverage. In this case, $H_0$ and $H_1$ are associated with BPH and SPH instances, respectively. D. Balanced ROC curves for BPH vs. SPH with matched and partially-matched reference panels of admixed embryos, varying depths of coverage. Here the randomly mismatched reference panel corresponds to either the parental or maternal ancestry.
Figure 12B:
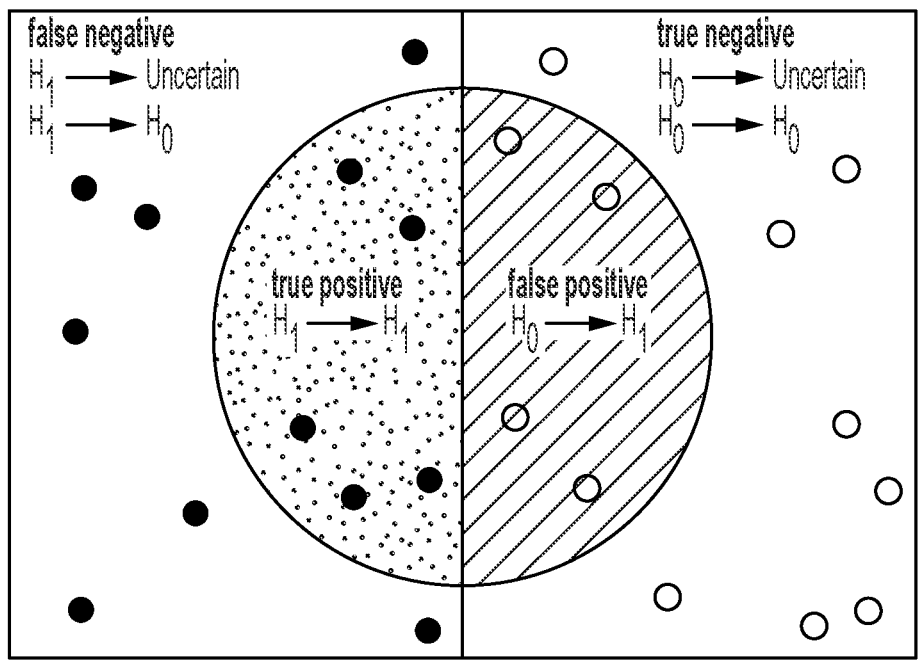

In order to benchmark and optimize LD-PGTA, we developed a generalization of the ROC curve for scenarios that include an ambiguous class (i.e., bins with a confidence interval spanning zero), which we hereafter denote as the "balanced" ROC curve. For a given discrimination threshold, a balanced true (false) positive rate, denoted as BTPR (BFPR), is defined as the average of the true (false) positive rate of predicting BPH and SPH trisomy (FIGS. 12A and 12B). The balanced ROC curve thus depicts the relationship between the BTPR and BFPR at various confidence thresholds.

Figure 12C:
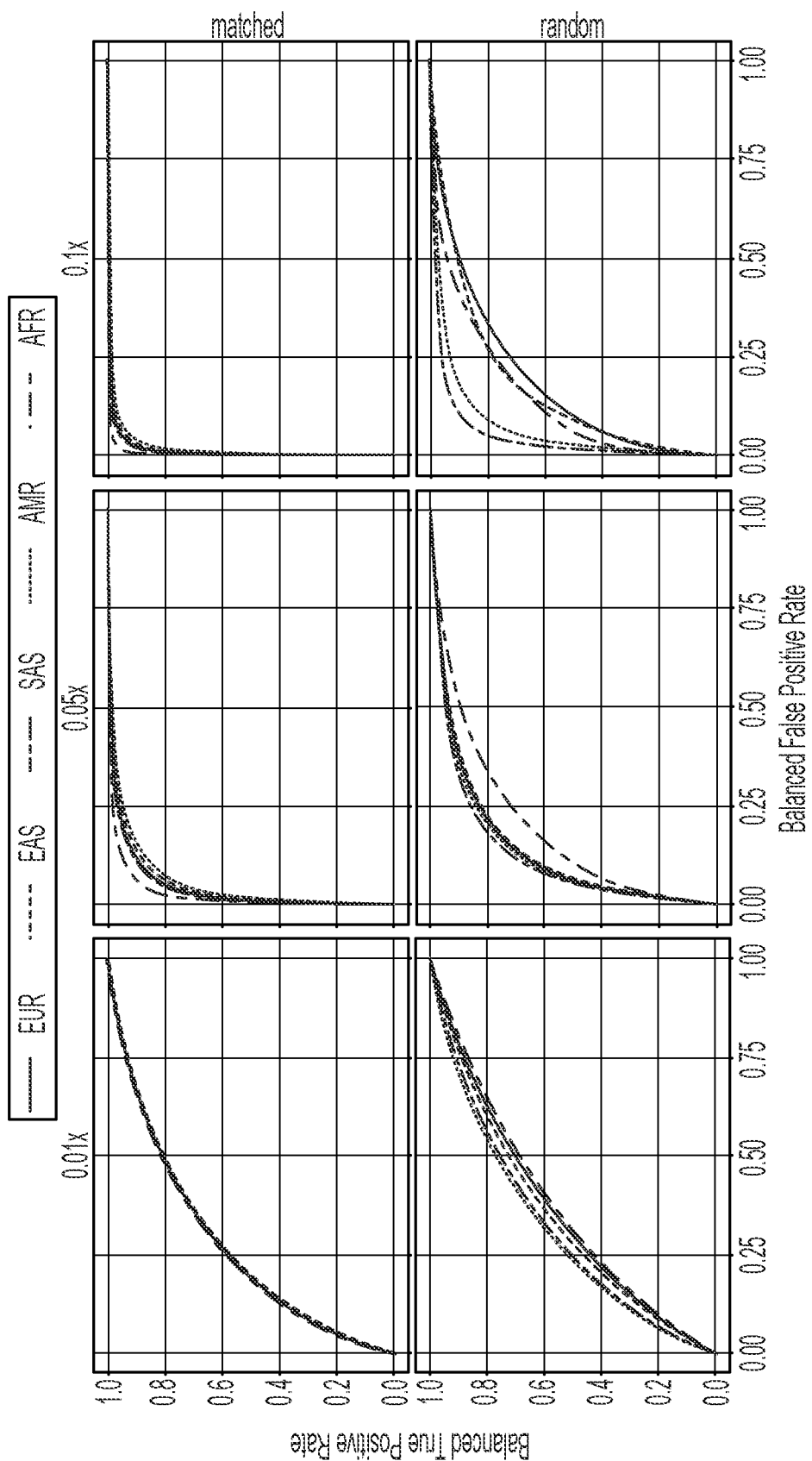

We generated balanced ROC curves for bins within simulated trisomic chromosomes (BPH and SPH) for samples of non-admixed ancestry and a correctly specified reference panel (FIG. 12C). At depths of 0.01×, 0.05× and 0.1×, LD-PGTA achieved a mean BTPR across ancestry groups of 33.4%, 88.6% and 97.5%, respectively, with a BFPR of 10%. Expanding our view across all classification thresholds, we found that the area under the balanced ROC curves was 0.73, 0.95 and 0.98 at depths of 0.01×, 0.05×0 and 0.1×, respectively. Our results thus demonstrate that as the depth of coverage increases from 0.01× to 0.1×, the balanced ROC curve approaches a step function, nearing ideal classification performance.

We also observed that short read lengths performed better than longer reads at low coverage. While counter-intuitive, this relationship arises due to the fact that coverage is a linear function of read length. Thus, holding coverage constant, a large number of shorter reads will achieve more uniform coverage than a small number of longer reads.

Evaluating Sensitivity to Ancestries of the Target Sample and Reference Panel We next extended our simulations to test the sensitivity of our classifier to specification of a reference panel that is appropriately matched to the ancestry of the target sample. Specifically, we simulated samples by drawing haplotypes from a reference panel composed of one of the five super-populations of the 1000 Genomes Project, then applied LD-PGTA while either specifying a reference panel composed of haplotypes from the same super-population (i.e., "matched") or from a mixture of all super-populations (i.e., "mismatched"). Notably, any phased genomic dataset of matched ancestry could be used in place of the 1000 Genomes Project dataset, with performance maximized in large datasets with closely matched ancestries.

While classification performance was high across all continental ancestry groups under the matched-ancestry scenario, performance moderately declined in all scenarios where the reference panel was misspecified (FIG. 12C). Due to such misspecification, the mean BTPR across ancestry groups declined by 8.9%, 28.3% and 31.0%, at a BFPR of 10% and depths of 0.01x, 0.05x and 0.1x, respectively. Moreover, the area under the balanced ROC curves decreased by 0.06, 0.10 and 0.11 at depths of 0.01x, 0.05x and 0.1x, respectively. Specification of a reference panel with rates of heterozygosity that exceeded those of the target sample resulted in a small bias in favor of the BPH hypothesis, while misspecification involving a reference panel with lower rates of heterozygosity than the target sample produced a small bias in favor of the SPH hypothesis.

Figure 12D:
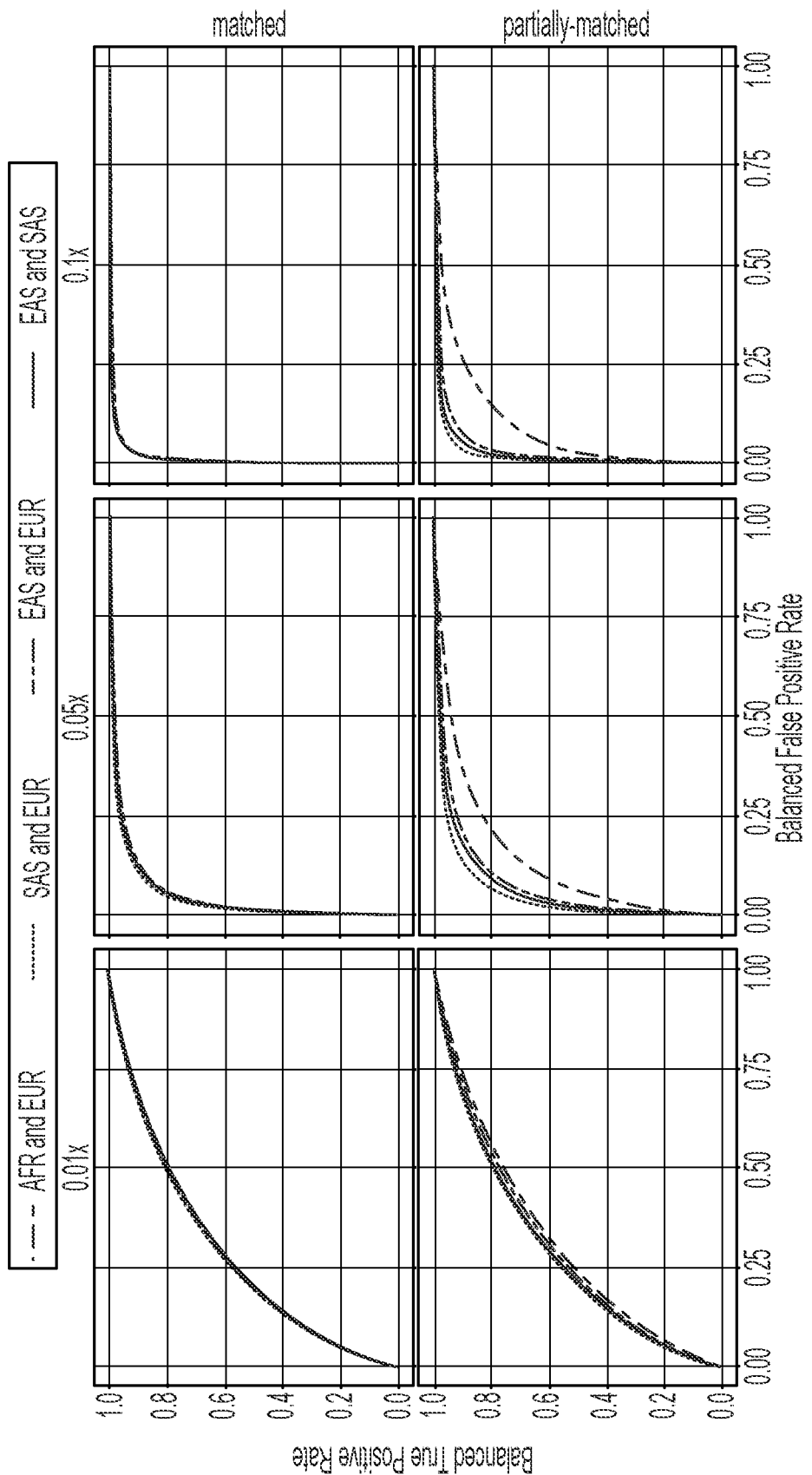

Seeking to test classification performance on individuals of admixed ancestries, we extended our simulation procedure to generate test samples composed of chromosomes drawn from distinct super-populations. In following with our previous analysis, we tested our method with and without correct specification of the component ancestries contributing to the admixture. Specifically, we implemented the latter scenario by specifying a single reference panel that matched the ancestry of either the maternal or paternal haplotypes (i.e., "partially-matched"; FIG. 12D). Our results demonstrated that the performance of LD-PGTA for correctly specified admixture scenarios was comparable to that observed for non-admixed scenarios. The ratio of mean AUC across ancestries and coverages for non-admixed samples versus admixed samples was 1.0. The impacts of reference panel misspecification were again greatest for admixed individuals with African ancestry, likely reflecting differences in structure of LD (shorter haplotypes) among African populations. For the African-European admixture scenario the BTPR decreased by 4.4%, 24.9% and 23.1% at a BFPR of 10% and depths of 0.01x, 0.05x and 0.1x when admixture was misspecified.

Application to PGT-A Data

We next proceeded to apply our method to existing data from PGT-A, thereby further evaluating its performance and potential utility under realistic clinical scenarios. Data were obtained from IVF cases occurring between 2015 and 2020 at the Zouves Fertility Center (Foster City, USA). Embryos underwent trophectoderm biopsy at day 5 post-fertilization, followed by PGT-A using the Illumina VeriSeq PGS kit and protocol, which entails sequencing on the Illumina MiSeq platform (36 bp single-end reads). The dataset comprised a total of 8153 embryo biopsies from 1640 IVF cases, with maternal age ranging from 22 to 56 years (median =38). Embryos were sequenced to a median coverage 0.0083xper sample, which we note lies near the lower limit of LD-PGTA and corresponds to an expected false positive rate of >0.14 at a 50% confidence threshold for classification of SPH and BPH trisomy.

Ancestry Inference for Reference Panel Selection

Given the aforementioned importance of the ancestry of the reference panel, we used LASER to perform automated ancestry inference of each embryo sample from the low-coverage sequencing data. LASER applies principal components analysis (PCA) to genotypes of reference individuals with known ancestry. It then projects target samples onto the reference PCA space, using a Procrustes analysis to overcome the sparse nature of the data. Ancestry of each target sample is then deduced using a k-nearest neighbors approach.

Figure 13B:
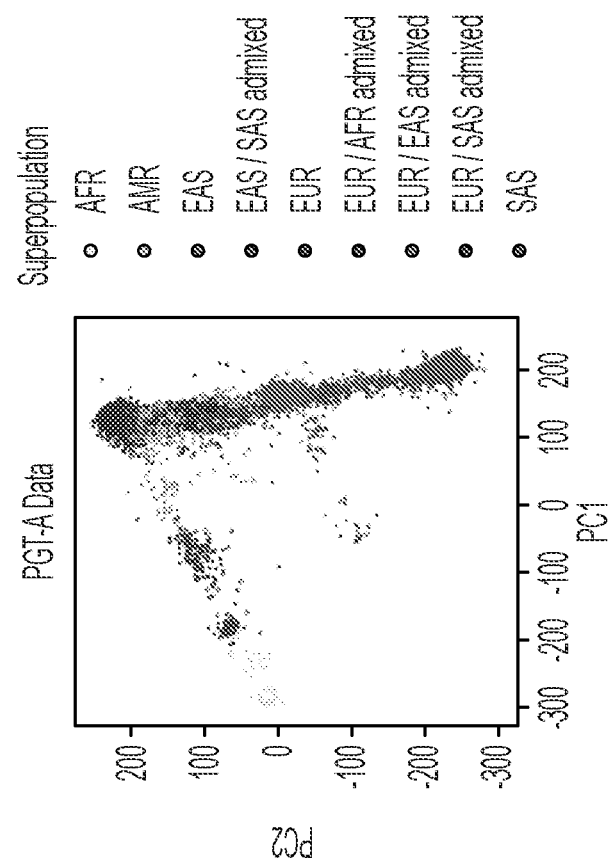
FIG. 13 (Panels A-D). Ancestry inference from low-coverage PGT-A data informs the selection of matched reference panels. Principal component axes were defined based on analysis of 1000 Genomes reference samples (panels A and C), and colored according to superpopulation annotations. First-generation admixed reference samples were simulated by computing the mean of random samples from each of the component superpopulations. Low-coverage embryo samples were then projected onto these axes using a Procrustes approach implemented with LASER (v2.0) (panels B and D) and their ancestries were classified using k-nearest neighbors of the first four principal component axes (k=10). Panels A and B depict principal components 1 and 2, while panels C and D depict principal components 2 and 3, together capturing continental-scale patterns of global ancestry.
Figure 13A:
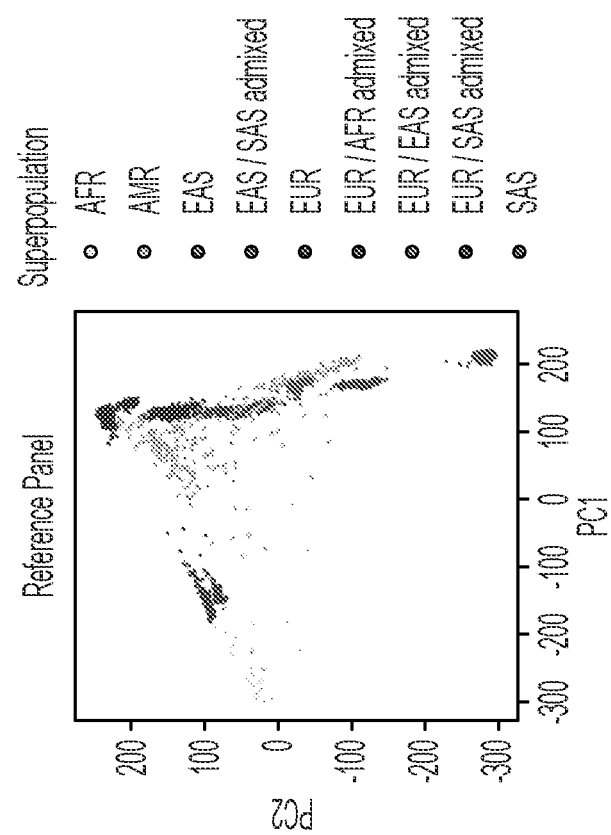
Figures 13C, 13D:
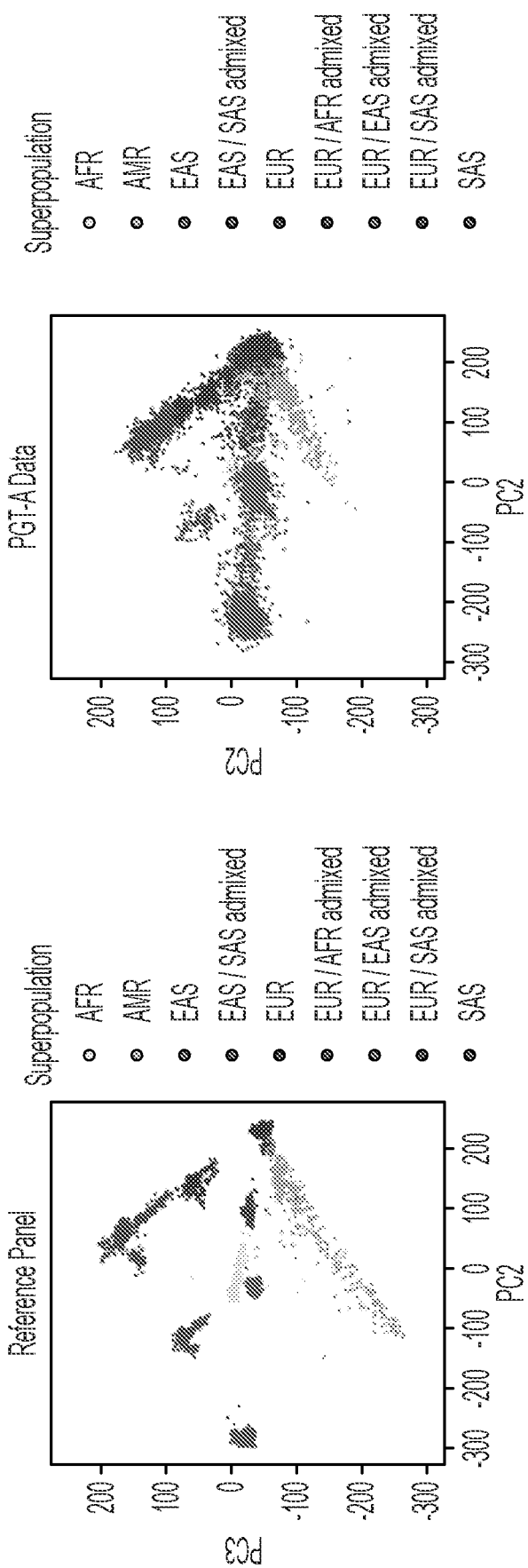

Our analysis revealed a diverse patient cohort, consistent with the demographic composition of the local population (FIG. 13). Specifically, we inferred a total of 2037 (25.0%) embryos of predominantly East Asian ancestries, 900 (11.0%) of South Asian ancestries, 2554 (31.3%) of European ancestries, 669 (8.2%) of admixed American ancestries, and 44 (0.5%) of African ancestries, according to the reference panels defined by the 1000 Genomes Project. Interestingly, we also observed 1936 (23.7%) embryos with principal component scores indicating admixture between parents of ancestries from one of the aforementioned super-populations, which we thus evaluated using the generalization of PGT-A for admixed samples. More specifically, we inferred a total of 1264 (15.5%) embryos to possess admixture of East Asian and European ancestries, 447 (5.5%) of South Asian and European ancestries, 129 (1.6%) of East and South Asian ancestries and 96 (1.2% of African and European ancestries. The ancestry of 13 (0.2%) embryos remained undetermined.

Preliminary Analysis With a Coverage-Based Classifier

Ploidy status of each chromosome from each embryo biopsy was first inferred using the Illumina BlueFuse Multi Software suite in accordance with the VeriSeq protocol. Similar in principle to several open source tools, BlueFuse Multi detects aneuploidies based on the coverage of reads aligned within 2500 bins that are distributed along the genome, normalizing and adjusting for local variability in GC content and other potential biases. It then reports the copy number estimates for each bin (as a continuous variable), as well as the copy number classification of each full chromosome (as a "gain", "loss", or neither), as well as numerous auxiliary metrics to assist with quality control.

Figure 14C:
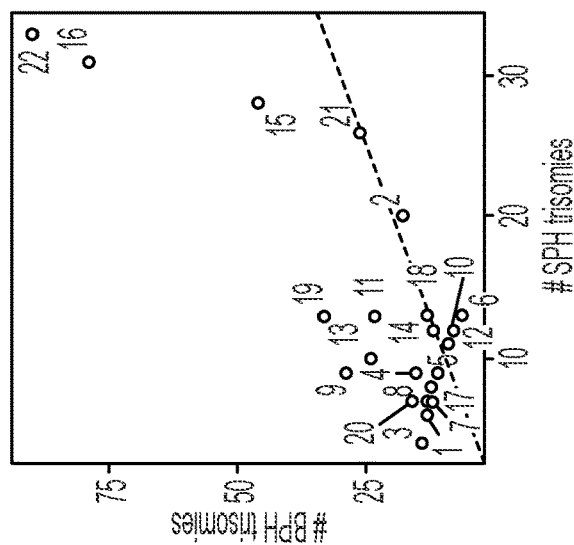
FIG. 14 (Panels A-C). Application of LD-PGTA to low-coverage sequencing-based data. A. LD-PGTA was used to refine classification results from 4331 chromosomes originally diagnosed as aneuploid based on standard coverage-based methods (i.e., Bluefuse Multi), including strong validation of putative monosomies, as well as subclassification of BPH and SPH trisomies. B. Association of BPH and SPH trisomies with maternal age. C. LD-PGTA classifications of BPH versus SPH trisomy, stratifying by individual chromosome. BPH trisomy is strongly enriched on chromosomes 16 and 22, while signatures of SPH trisomy are more evenly distributed among the various autosomes. Chromosomes were classified using a 50% confidence interval, corresponding to a false positive rate of >0.14.
Figure 14B:
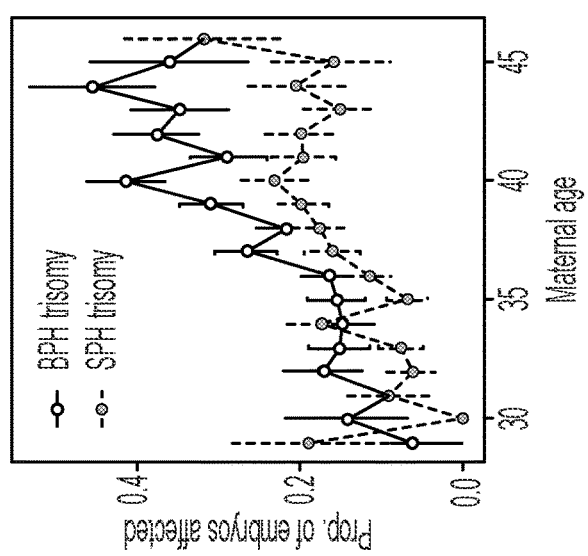
Figure 14A:
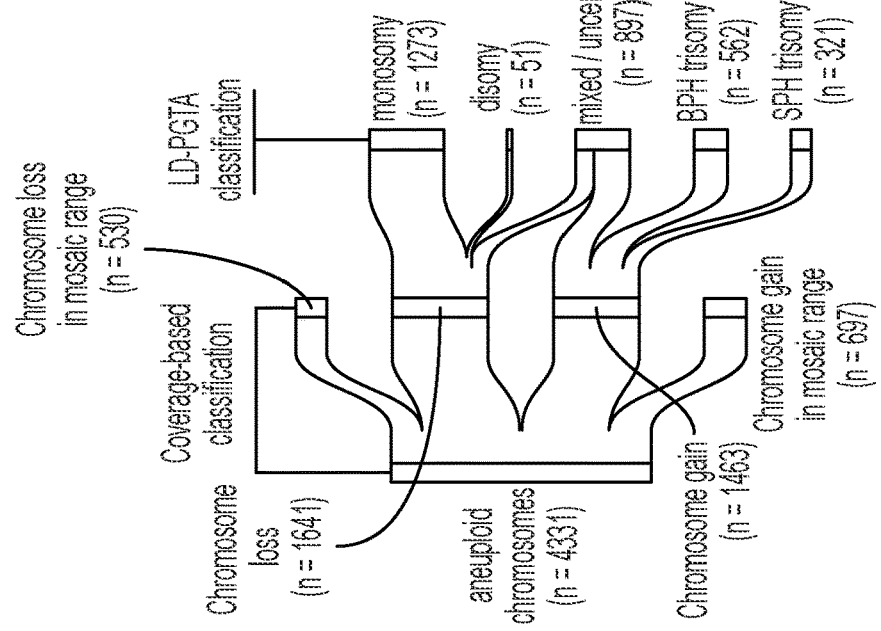

Of the original 8153 embryos, we excluded 138 embryos with low signal-to-noise ratios (Derivative Log Ratio [DLR] 0.4), as well as an additional 969 embryos with low coverages that were unsuitable for analysis with LD-PGTA (mean coverage<0.005x). This resulted in a total of 7046 embryos used for all downstream analyses. Aggregating the BlueFuse Multi results from these embryos, we identified 2551 embryos that were classified as aneuploid (36.2%), including 524 (7.4%) with single-chromosome gains, 701 (9.9%) with single-chromosome losses, and 670 (9.5%) with aneuploidies involving 2 or more chromosomes. A total of 777 (11.0%) embryos possessed one or more chromosomes in the mosaic range, including 310 (4.4%) embryos that also harbored non-mosaic aneuploidies. The rate of aneuploidy was significantly associated with maternal age (Quasibinomial GLM: $\hat{\beta}$age=0.0945, SE=0.0077, P<1×10$^{-10}$), replicating well described patterns from the literature. On an individual chromosome basis, the above results correspond to a total of 2171 chromosome losses (1641 complete and 530 in the mosaic range) and 2160 chromosome gains (1463 complete and 697 in the mosaic range) (FIG. 14A). These conventional coverage-based results serve as the starting point for refinement and sub-classification with LD-PGTA.

Sub-Classification of Meiotic and Mitotic Trisomies

LD-PGTA is intended to complement coverage-based methods, using orthogonal evidence from genotype data to support, refute, or refine initial ploidy classifications. The relevant hypotheses for LD-PGTA to test are therefore based on the initial coverage-based classification. Applying LD-PGTA to the 1641 putative chromosome losses, we confirmed the monosomy diagnosis for 1273 (77.6%) chromosomes, designated 317 as ambiguous (i.e., 50% confidence interval spanning 0), and obtained conflicting evidence favoring disomy for 317 chromosomes (3.1%). We note that the latter group is within the expected margin of error (FPR=XXX) if all 1641 chromosomes were in fact monosomic, given the selected confidence threshold of 50%.

Seeking to better understand the molecular origins of trisomy, we next applied LD-PGTA to the 1463 originally diagnosed chromosome gains. This revealed a total of 562 (38.4%) chromosomes exhibiting evidence of BPH trisomy (i.e., meiotic origin), 321 (21.9%) chromosomes exhibiting evidence of full SPH trisomy (i.e., mitotic origin or meiotic origin lacking recombination), and 580 (39.6%) chromosomes exhibiting evidence of a mixture of BPH and SPH tracts (i.e., meiotic origin with recombination) or uncertain results. Intriguingly, we observed that BPH trisomies exhibited a nominally stronger association with maternal age than SPH trisomies, consistent with previous literature demonstrating a maternal age effect on meiotic but not mitotic aneuploidy, though the difference was not statistically significant (Quasibinomial GLM: $\hat{\beta}_{age \times BP\ H/SP\ H}=-0.0106$, SE=0.0181, P=0.558; FIG. 14B). Moreover, chromosomes 16 (binomial test: $P=5.3\times10^{-6}$) and 22 (binomial test: $P=2.7\times10^{-7}$) were strongly enriched for BPH versus SPH trisomies, again consistent with a known predisposition of these two chromosomes to mis-segregation maternal meiosis, including based on their strong maternal age effect (FIG. 14C).

Figure 15B:
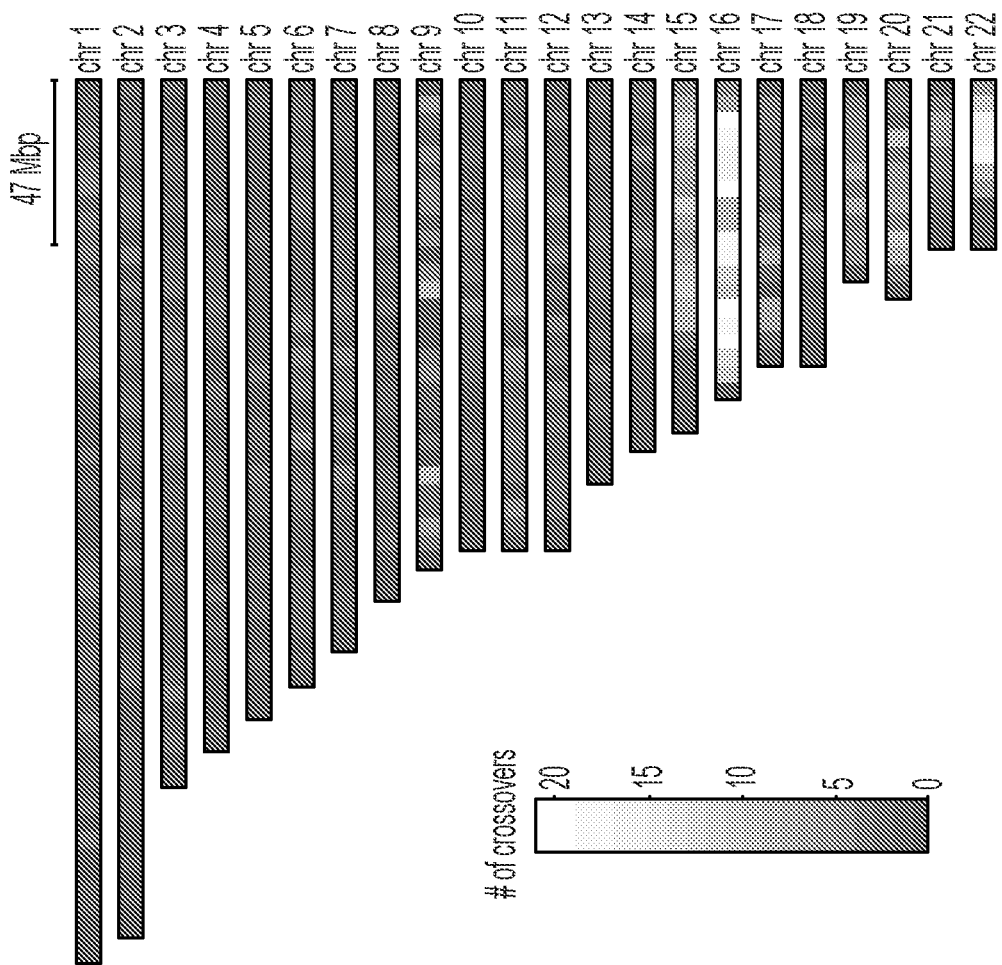
FIG. 15 (Panels A and B).
Figure 15A:
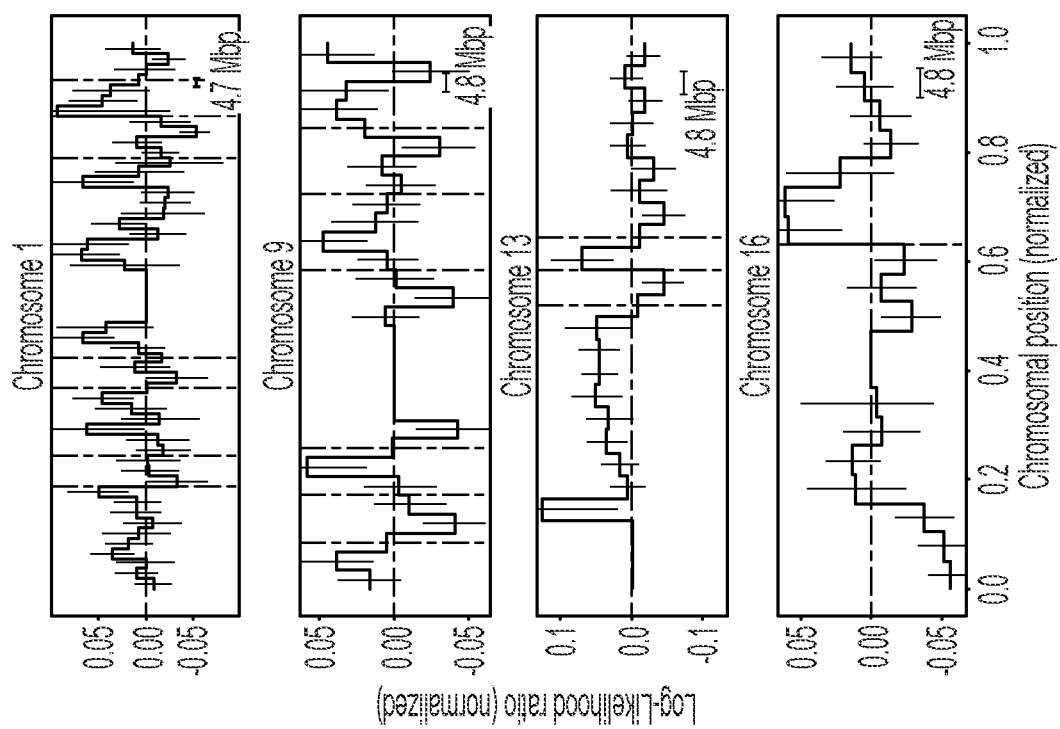

Scanning along consecutive bins across a trisomic chromosome, switches between tracts of BPH and SPH trisomy indicate the occurrence of recombination, offering a method for mapping meiotic crossovers and studying their role in the genesis of aneuploidy. Although the low coverage of this particular dataset offered very coarse resolution to this end (~5 Mbp), we nevertheless identified 1070 putative meiotic crossovers and mapped their heterogeneous distribution across XXX trisomic chromosomes (conditioning on coverage >0.01×; 70% confidence threshold; FIG. 15).

Hidden Abnormalities in Genome-Wide Ploidy

Because of their reliance on differences in normalized coverage of reads aligned to each chromosome, sequencing-based implementations of PGT-A are typically blind to haploidy, triploidy, and other potential genome-wide aberrations. While differences in coverage between the X and Y chromosome may offer a clue about certain forms of triploidy, this scenario does not apply to haploidy or to forms of triploidy where the Y chromosome is absent. Moreover, even when present, the short length of the Y chromosome diminishes the ratio of signal to noise and limits its diagnostic utility. As such, haploid and triploid embryos (especially those lacking Y chromosomes) are routinely misclassified as diploid by coverage-based methods for PGT-A analysis.

In order to overcome these challenges, we generalized LD-PGTA to detect abnormalities in genome-wide ploidy, effectively combining evidence for or against specific chromosome abnormalities across the entire genome. In the case of haploidy, this entailed aggregating the LLRs of the comparison between disomy and monosomy across all genomic bins, while in the case of triploidy, we aggregated the LLRs of the comparison between disomy and BPH trisomy across all genomic bins. Because the chromosomes of triploid samples will possess tracts of both BPH and SPH trisomy, our power for detection is lower than for haploidy, and it thus requires a less stringent threshold (see Methods).

Figure 16A:
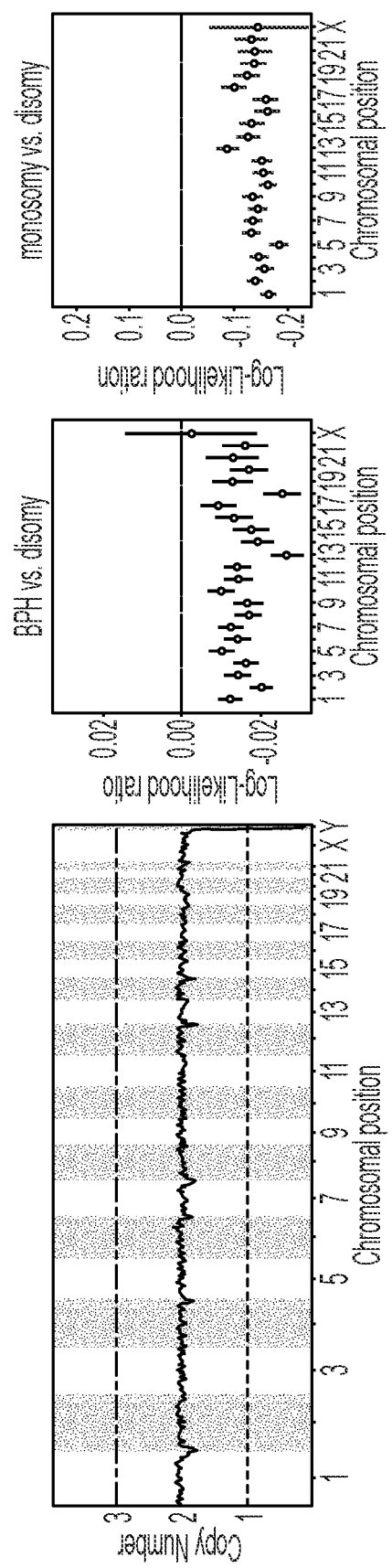
FIG. 16 (Panels A-C). Visualization of results from representative putative diploid (A.), triploidy (B.), and haploid (C.) samples. Copy number estimates obtained using a standard coverage-based approach (BlueFuse Multi) are depicted in the left column and are indicative of diploidy. LD-PGTA results are depicted in the right two columns and suggest genome-wide abnormalities in ploidy for the latter two samples.
Figure 16B:
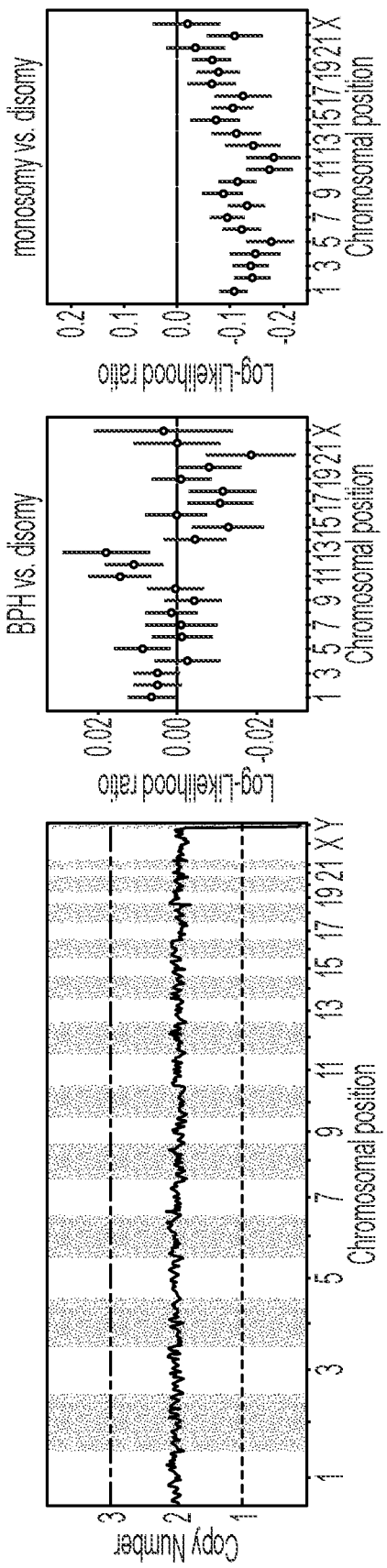
Figure 16C:
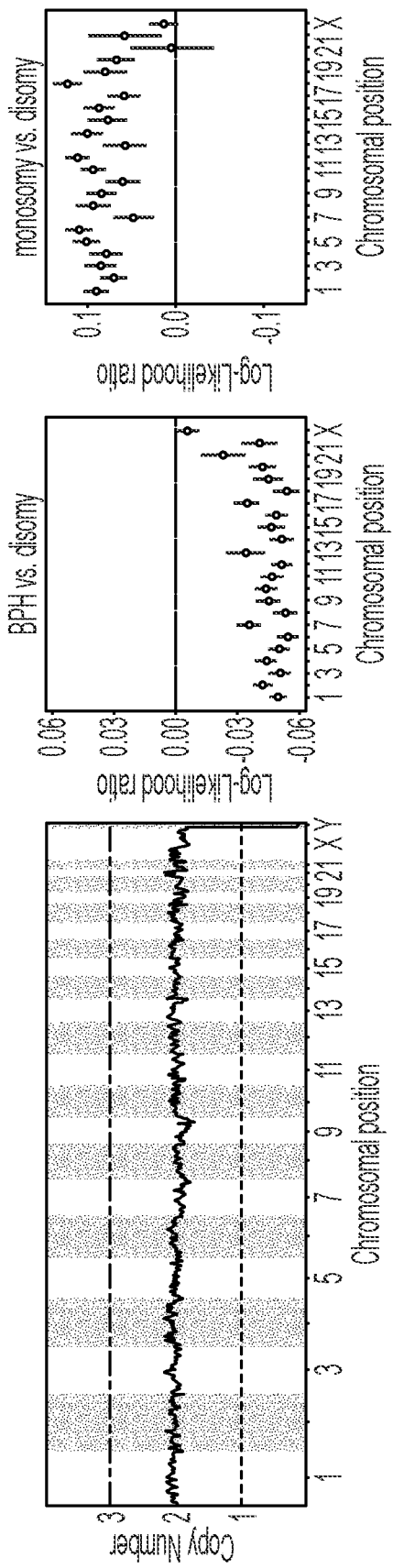

We started our analysis with the 4495 embryos that were initially classified as euploid based on conventional coverage-based tests (i.e., Bluefuse Multi). To take a more conservative approach, we applied additional filtering to consider only embryos with >0.07× and >0.03× with at least 1000 and 250 informative genomic windows for the classification of triploidy and haploidy, respectively. In the case of triploidy, this confined the initial pool of embryos to XXX, among which we identified 12 (X %) as likely triploid (see Methods; Eq. 24; FIG. 16). In the case of haploidy, our stringent filtering criteria restricted our analysis to an initial pool of XXX embryos, among which we identified 12 (X %) as likely haploid (see Methods; Eq. 11; 8). Of the 12 putative triploid embryos, 5 (42%) exhibited an XXX composition of sex chromosomes. In contrast, all of the haploid embryos possessed an X chromosome and no Y chromosome, consistent with previous studies of IVF embryos that suggested predominantly gynogenetic origins of haploidy, both in the context of intracytoplasmic sperm injection (ICSI) and conventional IVF. Among the 12 putative triploid embryos, we observed 5 embryos with coverage-based signatures of XXY sex chromosome complements. Moreover, 6 of the 12 embryos which we classified as haploid were independently noted as possessing only a single pronucleus (i.e., monopronuclear or 1 PN) at the zygote stage upon retrospective review of notes from the embryology lab. Importantly, however, microscopic assessment of pronuclei is known to be prone to error and is imperfectly associated with ploidy status and developmental potential. Nevertheless, these results offer independent validation of our statistical approach, which may be used to flag diploid-testing embryos as harboring potential abnormalities in genome-wide ploidy.

DISCUSSION

Aneuploidy affects more than half of human embryos and is the leading cause of pregnancy loss and IVF failure. PGT-A seeks to improve IVF outcomes by prioritizing euploid embryos for transfer. Current low-coverage sequencing-based implementations of PGT-A rely entirely on comparisons of the depth of coverage of reads aligned to each chromosome. In such low coverage settings, genotype observations are so sparse that they are typically regarded as uninformative.

Here we showed that by leveraging patterns of LD, even sparse genotype data are sufficient to capture signatures of aneuploidy, especially when aggregating over large genomic intervals such as entire chromosomes. In doing so, our method, termed LD-PGTA, reveals additional information that is hidden to standard coverage-based analyses of PGT-A data, including the designation of meiotic and mitotic trisomies, as well as the discovery of errors in genome-wide ploidy (i.e., haploidy and triploidy). Using simulations, we demonstrated the high accuracy of LD-PGTA even at the extremely low depths of coverage (0.05×). We then showcased the utility of our method through application to an existing PGT-A dataset composed of 7046 IVF embryos, stratifying trisomies of putative meiotic and mitotic origin, and reclassifying 12 presumed diploid embryos as haploid and an additional 12 as triploid.

The key innovation of LD-PGTA is the use of allele frequencies and patterns of LD as measured in an external reference panel such as the 1000 Genomes Project. Because these parameters vary across human populations, the accuracy of our method depends on the correct specification of the reference panel with respect to the ancestry of the target sample. This challenge is analogous to that described in several recent studies investigating the portability of polygenic scores between populations, which are similarly biased by population differences in allele frequencies and patterns of LD. In contrast to polygenic scores, however, our simulations suggest that the practical effects of reference panel misspecification on aneuploidy classification are typically modest. Moreover, our analysis of PGT-A data demonstrates that even at very low depths of coverage, existing extensions of principal components analysis are sufficient to infer sample ancestries and guide the selection of an appropriate matched reference panel.

The genomic resolution of LD-PGTA is a function of multiple factors, including technical variables such as depth and evenness of sequencing coverage, read lengths, and desired confidence level, as well as a biological variables such as the magnitudes of local LD and genetic variation. The low genetic diversity of human populations ($\pi \approx 0.01$) is particularly limiting, even with increased sequencing coverage. In practice, an average coverage of 0.01× offers resolution of ~1 Mb, which corresponds to 46 non-overlapping windows on the shortest human chromosome. At higher depths of coverage (~0.5×), our method permits the mapping of points of transition between different ploidy configurations. Depending on the particular hypotheses under consideration, such transitions could reflect evidence of segmental aneuploidies or—in the case of BPH and SPH trisomy—allow the mapping of meiotic crossover breakpoints on trisomic chromosomes. Beyond the clinical applications previously discussed, this novel output of our method will facilitate future research into the factors influencing meiotic recombination, as well as its impacts on aneuploidy formation—topics of longstanding interest in basic reproductive biology.

Standard sequencing-based implementations of PGT-A infer the copy number of each chromosome based on variation in the local depth of coverage, and typically support coverages as low as 0.005×. In contrast, LD-PGTA requires mean coverage of approximately 0.05× to yield high accuracy for any individual embryo, as demonstrated by simulations across a wide range of coverage, read length, and ancestry and admixture scenarios. Nevertheless, when applied to large datasets such as that investigated in our study, global patterns emerge at even lower coverage that offer rough stratification of meiotic and mitotic errors and provide insight into the biological origins of aneuploidy, beyond the binary classification of aneuploid and euploid. As costs of sequencing continue to plummet, application of the method to higher coverage datasets and additional stages of development will further unlock its potential for both research and diagnostic aims.

We envision our method complementing rather than supplanting current coverage-based approaches to PGT-A, whose performance remains superior for tasks such as classification of monosomies and trisomies of one or few chromosomes. Meanwhile, the application of LD-PGTA can be used to flag haploidies or triploidies that remain invisible to current coverage-based approaches. Additionally, the subclassification of meiotic and mitotic trisomies may prove valuable as orthogonal evidence to distinguish potentially viable mosaic embryos from those possessing lethal meiotic errors. This knowledge is particularly relevant to the many patients with no euploid-testing embryos available for transfer. Together, our method offers a novel approach for extracting valuable hidden information from standard preimplantation and prenatal genetic testing data, toward the goal of improving pregnancy outcomes.

METHODS

Prioritizing Informative Reads

Broadly, our method overcomes the sparse nature of low-coverage sequencing data by leveraging LD structure of an ancestry-matched reference panel. Measurements of LD require pairwise and higher order comparisons and may thus grow intractable when applied to large genomic regions. To ensure computational efficiency, we developed a scoring algorithm to prioritize reads based on their potential information content, as determined by measuring haplotype diversity within a reference panel at sites that they overlap. We emphasize that the priority score of a read only depends on variation within the reference panel and not on the alleles that the read possesses. The score of a read is calculated as follows:

1. Based on the reference panel, we list all biallelic SNPs that overlap with the read and their reference and alternative alleles.
2. Using the former list, we enumerate all the possible haplotypes. In a region that contain n biallelic SNPs there are 2n possible haplotypes.
3. The frequency of each haplotype is estimated from the reference panel by computing the joint frequency of the alleles that comprise each haplotype.
4. We increment the priority score of a read by one for every haplotype with a frequency between $f_0$ and $1-f_0$.

An example of scoring a read that overlaps with three SNPs is described here (where $f_0=0.1$). The scoring metric is based the principle that reads that overlap with potentially informative SNPs with intermediate allele frequencies should receive high priority, as the inclusion of such sites will increase our ability to discern ploidy hypotheses. In the simplest case, where a read overlaps with only a single SNP, the score of the read would be two when the minor allele frequency (MAF) is at least $f_0$ and otherwise zero. We note that all observed alleles from the same read are considered as originating from the same underlying molecule. Thus, the score should reflect the number of common haplotypes existing in the population at the chromosomal region that overlaps with the read. For a reference panel on the scale of the 1000 Genomes Project (2500 individuals), 25%-45% of common SNPs have a nearest neighbor within 35 bp. Hence, even for short reads, the score metric must account for reads that span multiple SNPs.

Comparing Hypotheses With the Likelihood Ratio

By virtue of LD, observations of a set of alleles from one read may provide information about the probabilities of allelic states in another read that originated from the same DNA molecule (i.e., chromosome). In contrast, when comparing reads originating from distinct homologous chromosomes, allelic states observed in one read will be uninformative of allelic states observed in the other read. As different ploidy configurations are defined by different counts of identical and distinct homologous chromosomes, sparse genotype observations may provide information about the underlying ploidy status, especially when aggregated over large chromosomal regions. For a set of reads aligned to a defined genomic region, we compare the likelihoods of the observed alleles under four competing hypotheses:

1. A single copy of a chromosome, namely monosomy, which may arise by meiotic mechanisms such as non-disjunction, premature separation of sister chromatids, and reverse segregation or mitotic mechanisms such as mitotic non-disjunction and anaphase lag.
2. Two distinct homologous chromosomes, namely disomy, the outcome of normal meiosis, fertilization, and embryonic mitosis.
3. Two identical homologs with a third distinct homolog, denoted as SPH (single parental homolog). SPH may originate from mitotic error (FIG. 9) or rare meiotic errors without recombination.
4. Three distinct homologous chromosomes, denoted as BPH (both parental homologs). BPH observed in any portion of a chromosome is a clear indication of meiotic error (FIG. 9).

Our statistical models are based on the premise that the odds of two reads being drawn from the same haplo-type differ under the different scenarios. Specifically, for disomy, the odds are 1:1, for monosomy, the odds are 1:0, for BPH trisomy, the odds are 1:2, and for SPH trisomy, the odds are 5:4 (FIG. 10). If a pair of reads is drawn from identical homologs, the probability of observing the two alleles is given by the joint frequency of these two alleles (i.e., the frequency of the haplotype that they define) in the reference panel. In contrast, if a pair of reads is drawn from distinct homologs, then the probability of observing the two alleles is simply the product of the frequencies of the two alleles in the reference panel:

$$P_{monosomy}(A \wedge B) = f(AB), \quad (1)$$

$$P_{disomy}(A \wedge B) \frac{1}{2} f(AB) + \frac{1}{2} f(A) f(B), \quad (2)$$

$$P_{SPH}(A \wedge B) = \frac{5}{9} f(AB) + \frac{4}{9} f(A) f(B), \quad (3)$$

$$P_{BPH}(A \wedge B) = \frac{1}{3} f(AB) + \frac{2}{3} f(A) f(B). \quad (4)$$

where f(A) and f(B) are the frequencies of alleles A and B in the population. Likelihoods of two of the above hypotheses are compared by computing a log-likelihood ratio:

$$\gamma(A, B) = \log \frac{P_{hypothesis\ 1}(A \wedge B)}{P_{hypothesis\ 0}(A \wedge B)} \quad (5)$$

When a read overlaps with multiple SNPs, f(A) should be interpreted as the joint frequency of all SNP alleles that occur in read A (i.e., the frequency of haplotype A). Similarly, f(AB) would denote the joint frequency of all SNP alleles occurring in reads A and B. The equations above were extended to consider up 18 reads per window, as described in the later section "Generalization to arbitrary ploidy hypotheses". Estimates of allele and haplotype frequencies from a reference panel do not depend on theoretical assumptions, but rely on the idea that the sample is randomly drawn from a population with similar ancestry. One limitation, which we consider, is that reliable estimates of probabilities near zero or one require large reference panels. In practice, it is sufficient to construct the reference panels using statistically phased genotypes from surveys of human genetic diversity, such as the 1000 Genome Project.

Quantifying Uncertainty by Bootstrapping

To quantify uncertainty in our likelihood estimates, we performed m over n bootstrapping by iteratively resampling reads within each window. Resampling was performed without replacement to comply with the assumptions of the statistical models about the odds of drawing two reads from the same haplotype. Thus, in each iteration, only subsets of the available reads can be resampled. Specifically, within each genomic windows, up to 18 reads with a priority score exceeding a defined threshold are randomly sampled with equal probabilities. The likelihood of the observed combination of SNP alleles under each competing hypothesis is then calculated, and the hypotheses are compared by computing a log-likelihood ratio (LLR). The sample mean and the unbiased sample variance (i.e., with Bessel's correction) of the LLR in each window are calculated by repeating this process using a bootstrapping approach, $$\overline{\gamma}^{(w)} = \frac{1}{m} \sum_{s \in w} \gamma_s, \quad (6)$$

$$\mathrm{Var}(\gamma^{(w)}) = \frac{1}{m-1} \sum_{s \in w} (\gamma_s - \overline{\gamma}^{(w)})^2 \quad (7)$$

where $\gamma_s$ is the the log-likelihood ratio for s-th subsample of reads from the w-th genomic window and m is the number of subsamples. Because the number of terms in the statistical models grow exponentially, we subsample at most 18 reads per window. Moreover, accurate estimates of joint frequencies of many alleles requires a very large reference panel. Given the rate of heterozygosity in human populations and the size of the 1000 Genomes dataset, 18 reads is generally sufficient to capture one or more heterozygous SNPs that would inform our comparison of hypotheses.

Aggregating Log Likelihood Ratios Across Consecutive Windows

Even when sequences are generated according to one of the hypotheses, a fraction of genomic windows will emit alleles that do not support that hypothesis and may even provide modest support for an alternative hypothesis. This phenomenon is largely driven by the sparsity of the data as well as the low rates of heterozygosity in human genomes, which together contribute to random noise. Another possible source of error is a local mismatch between the ancestry of the reference panel and the tested sequence. Moreover, technical errors such as spurious alignment and genotyping could also contribute to poor results within certain genomic regions (e.g. near the centromeres). To overcome this noise, we binned LLRs across consecutive genomic windows, thereby reducing biases and increasing the classification accuracy at the cost of a lower resolution. Specifically, we aggregated the mean LLRs of genomic windows within a larger bin, $$\Gamma_{bin} = \sum_{w \in bin} \overline{\gamma}^{(w)}, \quad (8)$$

where $\bar{\gamma}(w)$ is the mean of the LLRs associated with the w-th genomic window. In addition, using the Bienayme formula, we calculated the variance of the aggregated LLRs, $$\mathrm{Var}(\Gamma_{bin}) = \sum_{w \in bin} \mathrm{Var}(\gamma^{(w)}), \qquad (9)$$

where $\mathrm{Var}(\gamma^{(w)})$ is the variance of the LLRs associated with a the w-th window. For a sufficiently large bin, the confidence interval for the aggregated LLR is $\Gamma\mathrm{bin} \pm z \sqrt{\mathrm{Var}(\Gamma\mathrm{bin})}$, where $z = \phi^{-1}(1-\alpha)$ is the z-score, $\phi$ is the cumulative distribution function of the standard normal distribution and $C = 100(1-2\alpha)\%$ is the confidence level. The confidence level is chosen based on the desired sensitivity vs. specificity. We normalized the aggregated LLRs by the number of genomic windows that comprise each bin, $\gamma\mathrm{bin} = \Gamma\mathrm{bin}/g$. Thus, the variance of the mean LLR per window is $\mathrm{Var}(\gamma\mathrm{bin}) = \mathrm{Var}(\gamma\mathrm{bin})/g^2$. These normalized quantities can be compared across different regions of the genome, as long as the size of the genomic window is the same on average.

Determining Optimal Window Size

To ensure sufficient data for bootstrap resampling, each genomic window should contain at least one read more than the number of reads in each bootstrap sample. We chose the size of the bootstrap sample as well as the number of bootstrap iterations according to the depth of coverage. Then, we calculated the number of required reads per window and accordingly adjusted the size of the genomic windows.

Pairwise LD in human genomes decays to a quarter of its maximal value over physical distances of 100 kbp, on average. Thus, when (a) the distance between consecutive observed alleles exceed 100 kbp or (b) a genomic window reaches 350 kbp and does not meet the minimal required number of reads, it is dismissed. An adaptive sliding window possesses advantages over a fixed length window in that it (a) accounts for GC-poor and GC-rich regions of a genome, which tend to be sequenced at lower depths of coverage using Illumina platforms and (b) accounts for varying densities of SNPs across the genome.

Simulating Meiotic- and Mitotic-Origin Trisomies

To simulate trisomies, we constructed synthetic samples comprised of combinations of three sampled phased haplotypes from the 1000 Genomes Project. These phased haplotypes were generated from VCF files to effectively form a pool of haploid sequences from which to draw trisomies.

We first assigned full chromosomes or chromosome segments to BPH or SPH trisomy states. We note that true meiotic trisomies exhibit a mixture of BPH and SPH segments, while mitotic trisomies exhibit SPH over their entire length. The BPH and SPH regions of simulated trisomic chromosomes were determined as follows:

1. We assumed that the number of transitions between BPH and SPH regions was equal to the number of meiotic crossover events, on average, per autosome. Thus, for chromosomes 1-6, 7-12 and 13-22 we simulated are 3,2 and 1 transition, respectively.
2. When simulating trisomies of meiosis II origin, we required that the region around the centromere reflect the SPH hypothesis.
3. For simplicity, we assumed homogeneity in the frequency of meiotic crossovers throughout the genome (excluding centromeres), thus drawing transition points (between SPH and BPH) from a uniform distribution.

Reads were simulated by selected a random position along the chromosome from a uniform distribution, representing the midpoint of an aligned read with a given length. Based on the selected position, one out of the three haplotypes was drawn from a discrete distribution, $$f(h, x) = \begin{cases} p_1(x), & h = 1 \\ p_2(x), & h = 2 \\ p_3(x), & h = 3 \end{cases} \qquad (10)$$

where the probability of haplotype h depends on the position of the read, x. When the read overlaps with a BPH region, all three haplotypes have the same probability, $p_1 = p_2 = p_3$. For an SPH region, the first haplotype is twice as likely as the second haplotype, $p_2 = 2p_1$, while the third haplotype is absent, $p_3 = 0$.

From the selected haplotype, h, a segment of length l that is centered at the selected chromosomal position, x, is added to simulated data, mimicking the process of short-read sequencing. This process of generating simulated sequencing data is repeated until the desired depth of coverage is attained.

Evaluating Model Performance on Simulated Data

We developed a classification scheme to infer the ploidy status of each genomic bin. Each class is associated with a hypothesis about the number of distinct homologs and their degeneracy (i.e., copy number of non-unique homologs). To this end, we compare pairs of hypotheses by computing log likelihood ratios (LLRs) of competing statistical models. In general, the specific models that we compare are informed by orthogonal evidence obtained using standard coverage-based approaches to aneuploidy detection (i.e., tag counting).

The confidence interval for the mean LLR is $\gamma\mathrm{bin} \pm z \sqrt{\mathrm{Var}(\gamma\mathrm{bin})}$, and z is referred to as the z-score. Thus, we classify a bin as exhibiting support for hypothesis 1 when $$\bar{\gamma}_{bin} - z\sqrt{\mathrm{Var}(\bar{\gamma}_{bin})} > 0, \qquad (11)$$

and for hypothesis 0 when $$\bar{\gamma}_{bin} + z\sqrt{\mathrm{Var}(\bar{\gamma}_{bin})} < 0, \qquad (12)$$

where the first (second) criterion is equivalent to requiring that the bounds of the confidence interval lie on the positive (negative) side of the number line.

For a given depth of coverage and read length, we simulate an equal number of sequences generated according to hypothesis 0 and 1, as explained in the previous section. Based on these simulations, we generate two receiver operating characteristic (ROC) curves for each bin. The first ROC curve is produced by defining true positives as simulations where sequences generated under hypothesis 0 are correctly classified. For the second ROC curve, true positives are defined as simulations where sequences generated under hypothesis 1 are correctly classified. These two ROC curves can be combined into a single curve, which we term "balanced ROC curve". The balanced true and false positive rates for a bin are defined as $$BTPR = \frac{1}{2}\left(\frac{H_0 \text{ instances classified as } H_0}{H_0 \text{ instances}} + \frac{H_1 \text{ instances classified as } H_1}{H_1 \text{ instances}}\right), \quad (13)$$

$$BFPR = \frac{1}{2}\left(\frac{H_0 \text{ instances classified as } H_1}{H_0 \text{ instances}} + \frac{H_1 \text{ instances classified as } H_0}{H_1 \text{ instances}}\right), \quad (14)$$

where a Hi instance with i=1, 2 is a sequence that was generated under hypothesis i.

The balanced ROC curve is particularly suited for classification tasks with three possible classes: H0, H1 and undetermined. The undetermined class contains all instances that do not fulfill the criteria in eqs. (11) and (12), i.e., instances where the boundaries of the confidence interval span zero. This classification scheme allows us to optimize the classification of both H0 and H1 instances, at the expense of leaving undetermined instances. The advantage of this optimization is a reduction in the rate of spurious classification. To generate each curve, we varied the confidence level and the number of bins.

Generalization to Arbitrary Ploidy Hypotheses

While the aforementioned ploidy hypotheses (monosomy, disomy, SPH trisomy, and BPH trisomy) are most relevant to our study, our method can be generalized to arbitrary ploidy hypotheses and an arbitrary number of observed alleles. Consider m reads from an autosome with a copy number of n, containing I unique homologs. We list all the possible ways in which reads may emanate from the different homologs. For example, in the case of two reads, denoted by A and B, and two unique homologs, the list contains four configurations, i.e., ({A}, {B}), ({B}, {A}, {AB}, ). We assign a weight to each configuration in the list. The weight depends on the degeneracy of each homolog. For example, the presence of two identical homologs means that the degeneracy of this homolog is two.

For a each configuration, we list the number of reads that were assigned to each homolog along with the de generacy of these homologs. Moreover, the i th element in the list is (ri, di) where ri is the number of reads assigned to the i th homolog and di is the degeneracy of this homolog. We also note that for each configuration, the relations "'çl ri=m and "'çl di=n hold. Then the weight associated with a configuration is "'£i (di)ri. di =n hold. Then, the weight All configurations that share the same partitioning of reads, regardless of the homolog to which the subset was assigned, are grouped together. For example, in the case of two reads and two unique homologs there are two possible partitions, i.e., {(A), {B} and {{AB}, . We associate each partition of reads with the total weight of all the configurations that share the same partition. In the case of two reads from a chromosome with two unique homologs out of three, we have (AB, 5) and (A/B, 4).

Each partition together with its associated weight, contributed a term to the statistical model. The term is a product of a normalized weight and joint frequencies. The normalization factor is n-m and each joint frequency corresponds to a subset of reads, e.g., using the partitions list from the former example we obtain P(AB)=5/9f(AB)+4/9f(A)f(B).

Efficient Encoding of Statistical Models

The number of terms in the statistical models grows exponentially with the number of alleles, and it is thus necessary to write the models in their simplest forms and encode them efficiently.

In order to identify common multiples in the statistical model, we group partitions of reads according to their subset with the smallest cardinality. For example, the partitions {{A}, {B, C}, {D, E} and {{A}, {B, E}, {C, D} share the subset {A}, which correspond to the frequency f(A).

The partitioning of reads can be encoded efficiently using the occupation basis. In this representation, all reads are enumerated. Each subset of reads is represented by a binary sequence, where the i th element is one when the i th read is included in the subset and zero otherwise. In other words, bits in a binary sequence denote whether a read is included in the subset. For example, when the first two reads are associated with the same homolog and the third read is associated with another homolog then (1, 2), (3) corresponds to (0, 1, 1), (1, 0, 0).

Generalization to Admixed Ancestry Hypotheses

Admixed individuals constitute a considerable portion of contemporary societies, and indeed all genomes possess admixture at varying scales and degrees. Here we generalize the ploidy hypotheses to account for admixture between two defined populations. A chromosome in an individual of recently admixed ancestry resembles a mosaic of chromosomal segments, each derived from a particular ancestral population. Thus, generalized statistical models should account for the possibility of admixed ancestry in the selection of appropriate reference panels.

For brevity, we consider an individual of first-generation mixed ancestry. However, given that our classification approach is applied to genomic windows, the generalization is also naturally applicable to admixture events in earlier generations whereby ancestry tracts would be fragmented by meiotic recombination. In the case of monosomy, the observed homolog is equally likely to have originated from either of the two parental populations, $$P_{monosomy}(A \wedge B) = \frac{1}{2}[f_1(AB) + f_2(AB)], \quad (15)$$

where f1 and f2 are joint frequency distributions that are associated with each respective population. For disomy, each homolog is inherited from a parent deriving from a different population, $$P_{disomy}(A \wedge B) = \frac{1}{4}[f_1(AB) + f_1(A)f_2(B)] + (1 \leftrightarrow 2), \quad (16)$$

where $(1 \leftrightarrow 2)$ is equal to the sum of all the other terms in the expression with the indices 1 and 2 exchanged, e.g., f1(A)f2(B)+(1↔2)=f1(A)f2(B)+f2(A)f1(B). Considering SPH trisomy, the third non-unique homolog originated from either of the two ancestral populations with equal probability and thus, $$P_{SPH}(A \wedge B) = \frac{1}{2}P\left(A \wedge B \;\middle|\; \begin{array}{c}\text{non-unique homolog}\\\text{is paternal}\end{array}\right) + \quad (17)$$

$$\frac{1}{2}P\left(A \wedge B \;\middle|\; \begin{array}{c}\text{non-unique homolog}\\\text{is maternal}\end{array}\right) =$$

$$\frac{5}{18}f_1(AB) + \frac{2}{9}f_1(A)f_2(B) + (1 \leftrightarrow 2).$$

Similarly, for the BPH trisomy hypothesis we have $$P_{BPH}(A \wedge B) = \frac{1}{2}P\left(A \wedge B \;\middle|\; \begin{array}{c}\text{2 unique homologs} \\ \text{are paternal}\end{array}\right) + \tag{18}$$
$$\frac{1}{2}P\left(A \wedge B \;\middle|\; \begin{array}{c}\text{2 unique homologs} \\ \text{are maternal}\end{array}\right) =$$
$$\frac{1}{6}f_1(AB) + \frac{2}{9}f_1(A)f_2(B) + \frac{1}{9}f_1(A)f_1(B) + (1 \leftrightarrow 2).$$

Admixed Ancestry Hypotheses with an Arbitrary Number of Alleles

The monosomy, disomy and SPH trisomy statistical models for admixed individuals and an arbitrary number of reads can be obtained from the corresponding statistical models for non-admixed individuals. We start with a statistical model for a non-admixed individual, where the SPH model for 3 reads is $$P_{SPH}^{non-admixed}(A \wedge B \wedge C) = \tag{19}$$
$$\frac{1}{3}f_1(ABC) + \frac{2}{9}[f_1(AB)f_1(C) + f_1(AC)f_1(B) + f_1(BC)f_1(A)].$$

We re-express each term with arbitrary frequency distributions, i.e., f1→fi, f1 f1→fi fj. Then, we multiply the expression by (1−δi,j)/2 and sum over i and j. Here and in what follows, δi,j and Si,j,k are the Kronecker delta and a generalization, respectively, and are defined as reads, $$\delta_{i,j} = \begin{cases} 1, & i = j \\ 0, & i \neq j \end{cases}, \delta_{i,j,k} = \begin{cases} 1, & i = j = k \\ 0, & \text{else} \end{cases}. \tag{20}$$

Following these three steps, we obtain the admixed SPH model for 3 reads, $$P_{SPH}^{admixed}(A \wedge B \wedge C) = \tag{21}$$
$$\sum_{i,j=1}^{2} \frac{1-\delta_{ij}}{2}\left\{\frac{1}{3}f_i(ABC) + \frac{2}{9}[f_i(AB)f_j(C) + f_i(AC)f_j(B) + f_i(BC)f_j(A)]\right\}.$$

Statistical models of BPH trisomy for admixed individuals and an arbitrary number of reads can also be obtained from the corresponding statistical models for non-admixed individuals. We start with a statistical model for a non-admixed individual, where the BPH model for 3 reads is $$P_{BPH}^{non-admixed}(A \wedge B \wedge C) = \frac{1}{9}f_1(ABC) + \tag{22}$$
$$\frac{2}{9}[f_1(AB)f_1(C) + f_1(AC)f_1(B) + f_1(BC)f_1(A) + f_1(A)f_1(B)f_1(C)].$$

We continue by re-expressing each term with arbitrary frequency distributions, i.e., f1→fi, f1 f1→fi fj and f1 f1 f1→fi fj fk. Then, we multiply the expression by (1−δi,j,k)/6 and sum over i, j and k. In keeping with our previous example we obtain $$P_{BPH}^{admixed}(A \wedge B \wedge C) = \sum_{i,j,k=1}^{2} \frac{1-\delta_{ijk}}{6}\left\{\frac{1}{9}f_i(ABC) + \tag{23}\right.$$
$$\left.\frac{2}{9}[f_i(AB)f_j(C) + f_i(AC)f_j(B) + f_i(BC)f_j(A) + f_i(A)f_j(B)f_k(C)]\right\}$$

Accounting for the Rate of Heterozygosity

One important feature of likelihood ratios is that the ratio rather than individual likelihoods should be the focus of interpretation. When a read overlaps with a common SNP and the embryo is homozygous at this locus, the read is uninformative for distinguishing trisomy hypotheses. We address this limitation in several ways:

1. The number of reads required to distinguish trisomy hypotheses is largely determined by the rate of heterozygosity in human genomes. Informative (heterozygous) sites in the target sample are unknown a priori. Even sites of common variation in the reference panel will frequently be homozygous in the target sample, necessitating sampling of many reads to capture informative sites.
2. The probability of observing genetic differences between haplotypes increases with the length of the region investigated. All alleles observed within a single read necessarily originate from the same molecule. Our model accounts for the possibility that a read overlaps multiple SNPs, any one of which may be informative for distinguishing haplotypes. Longer reads thus provide direct readout of haplotypes, improving performance of our method.
3. We use a scoring algorithm to prioritize reads that overlap with diverse haplotypes within the a reference panel, as described in the scoring section of the Methods. It is worth emphasizing that at extremely low-coverages, rare alleles play an important role in distinguishing trisomy hypotheses. Thus, one should avoid narrowing the bandwidth, $\Delta f = 1-2f0$ of the scoring metric beyond what is necessary to ensure computational efficiency.
4. Because a window might not contain reads that overlap with heterozygous sites, we use binning to aggregate the mean LLR across multiple consecutive windows. This procedure, which reduces biases inherent to low-coverage sequence data, especially in species and populations with low heterozygosity, is described in the aggregation section of the Methods.

For both the BPH and SPH statistical models, we checked whether small changes in the degeneracies of the unique homologs can compensate for low rates of heterozygosity in triploids. For example, instead of three unique homologs with equal degeneracies, (1, 1, 1) one can consider the case (1.4, 1.2, 1), which is equivalent to (7, 6, 5). We observed that for statistical models of at least three reads, small changes of the degeneracies did not substantially affect the percentage windows that were correctly classified. This underscores the robustness of the statistical models and suggests that the number of unique homologs is the most important parameter defining each hypothesis. One implication is that our approach is less efficient at distinguishing SPH trisomy from disomy, as both scenarios involve two unique homologs (albeit in different proportions). We therefore emphasize that LD-PGTA is best considered as a complement to, rather than a replacement for, standard coverage-based methods.

Implications of Overlapping Reads

Even at extremely low coverage, the probability of two reads to overlap is not negligible. Although overlaps of two reads are not sufficient to distinguish between ploidy hypotheses, they reduce the complexity of the calculations:
1. When two different alleles are observed at the same SNP, it means that they necessarily originated from different haplotypes. Thus, eliminating some of the terms in the statistical models.
2. When the same allele is observed twice, it reduces the dimensionality of the joint frequency, e.g., f(AA)=f(A).

Mapping Meiotic Crossovers

Transitions between the BPH and SPH hypotheses along the chromosome indicate the locations of meiotic crossovers. We approximated each crossover location as the boundary point between two adjacent bins, where one is classified as BPH and the second as SPH. This approximation becomes more precise as the size of the bins is reduced and the confidence interval becomes smaller.

Detecting Haploidy and Triploidy

A key aim of our method is the reclassification of sequences that were initially identified as euploid by standard coverage based approaches (denoted here as the null hypothesis, $h_0$) as exhibiting potential abnormalities of genome-wide ploidy. Specifically, coverage-based methods are based on the correlation between the depth of coverage of reads aligned to a genomic region and the copy number of that region. In the cases of (near-) haploidy and triploidy, no such correlation is evident because (nearly) all chromosomes exhibit the same abnormality, resulting in erroneous classification.

To this end, following the binning procedure that was introduced in eqs. (8) and (9), we aggregate the LLRs of each genomic window along the entire genome. In order to identify haploids, we test for cases where the confidence interval lies on the positive side of the number line, as formulated in eq. (11).

In the idealized case where triploids are composed of entirely BPH sequence, triploids are easily distinguished from diploids. However, true cases of triploidy generally originate from retention of the polar body, leading to a more realistic scenario in which regions of BPH are relegated to the ends of chromosomes, while the rest of the genome exhibits SPH. The remedy is to introduce a binary classifier that assesses whether there is enough evidence of genome-wide BPH to question the hypothesis of genome-wide diploidy, $$\bar{\gamma}_{bin} z\sqrt{(\text{Var}(\bar{\gamma}_{bin}))} > 0, \qquad (24)$$

In other words, it is enough to show that the confidence interval spans the zero in order to classify the case as a triploid.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, devices, systems, computer readable media, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of conducting genetic testing of a test subject prior to transferring the test subject to a maternal patient, the method comprising:
   obtaining a biopsy comprising one or more cells from the test subject, wherein the test subject comprises a preimplantation embryo;
   producing a set of sequencing reads from nucleic acids obtained the biopsy;
   selecting, by a computer, sequencing reads obtained from the test subject that comprise nucleic acid variants within defined genomic windows to produce sets of observed test subject nucleic acid variants;
   obtaining, by the computer, joint allele frequencies and/or linkage disequilibrium patterns of corresponding nucleic acid variants observed in a reference subject population to produce sets of reference subject joint allele frequency and/or linkage disequilibrium pattern data;
   classifying the chromosome number status of the test subject as at least likely euploid using the sets of observed test subject nucleic acid variants and the sets of reference subject joint allele frequency and/or linkage disequilibrium pattern data, wherein classifying the chromosome number status of the test subject comprises determining at least one likelihood ratio of two competing ploidy hypotheses; and,
   transferring the test subject to the maternal patient, wherein the test subject is transferred in utero of the maternal patient.

2. A method of conducting genetic testing of a an embryo prior to transferring the embryo to a maternal patient, the method comprising:
   obtaining a biopsy comprising one or more cells from the embryo, wherein the embryo comprises a preimplantation embryo;
   producing a set of sequencing reads from nucleic acids obtained the biopsy;
   selecting, by a computer, within defined genomic windows, sequencing reads overlapping informative SNPs that tag common haplotype variation, wherein the sequencing reads are obtained from a biopsy of the embryo;
   obtaining, by the computer, joint frequencies of corresponding SNPs from a phased panel of ancestry-matched reference haplotypes;
   randomly, by the computer, selecting 2-16 sequencing reads;
   computing, by the computer, probabilities of observed alleles under competing trisomy hypotheses;
   determining that the embryo is at least likely euploid by comparing, by the computer, the hypotheses by computing a likelihood ratio and estimating a mean and variance by sub-sampling random sets of reads using a bootstrapping approach to distinguish between meiotic- and mitotic-origin aneuploidies for the embryo; and, transferring the embryo to the maternal patient, wherein the embryo is transferred in utero of the maternal patient.

3. A method of conducting genetic testing of a an embryo prior to transferring the embryo to a maternal patient, the method comprising:
obtaining a biopsy comprising one or more cells from the embryo, wherein the embryo comprises a preimplantation embryo;
producing a set of sequencing reads from nucleic acids obtained the biopsy;
receiving, by a computer, sequencing reads comprising sequence information from an aneuploid chromosome, wherein the aneuploid chromosome is from the embryo;
dividing, by the computer, the sequence information from the aneuploid chromosome into a plurality of linkage disequilibrium (LD) blocks or genomic windows (GWs);
selecting, by the computer, one or more of the sequencing reads corresponding to one or more of the plurality of LD blocks or GWs to produce a set of selected sequencing reads;
determining, by the computer, probabilities of observing the selected sequencing reads under a meiotic-origin model and under a mitotic-origin model to produce a set of probability data;
determining that the embryo at least likely lacks a meiotic-origin aneuploidy by aggregating, by the computer, log-likelihood ratios across the plurality of LD blocks or GWs to produce aggregated log-likelihood ratio using the set of probability data, wherein an aggregated log-likelihood ratio significantly greater than zero indicates that the aneuploid chromosome is a meiotic-origin aneuploidy, and wherein an aggregated log-likelihood ratio significantly less than zero indicates that the aneuploid chromosome is a mitotic-origin aneuploidy, thereby distinguishing between the meiotic- and the mitotic-origin aneuploidies; and,
transferring the embryo to the maternal patient, wherein the embryo is transferred in utero of the maternal patient.

4. The method of claim 1, further comprising performing whole genome sequencing of nucleic acids obtained from the test subject to produce the sequencing reads.

5. The method of claim 1, wherein the sequencing reads comprise a coverage of less than 2×, less than 1×, less than 0.50×, less than 0.25×, less than 0.15×, less than 0.10×, or less than 0.05× of a genome of the test subject.

6. The method of claim 1, wherein the chromosome number status comprises a state selected from the group consisting of: a monosomy, a monoploidy, a haploidy, a disomy, a diploidy, a trisomy, a triploidy, a tetrasomy, a tetraploidy, a pentasomy, a pentaploidy, and a mosaicisim.

7. The method of claim 1, wherein the chromosome number status comprises a meiotic-origin aneuploidy.

8. The method of claim 1, wherein the chromosome number status comprises a mitotic-origin aneuploidy.

9. The method of claim 1, comprising determining one or more both parental homologs (BPH) and/or one or more single parental homolog (SPH) signatures for the test subject.

10. The method of claim 2, wherein a probability that two sequencing reads are obtained from an identical haplotype under the meiotic-origin model is 1/3.

11. The method of claim 2, wherein a probability that two sequencing reads are obtained from an identical haplotype under the mitotic-origin model is 5/9.

12. The method of claim 2, comprising determining whether an aneuploidy is due to a meiosis I error or a meiosis II error when the aneuploid chromosome is a meiotic-origin aneuploidy.

13. The method of claim 2, wherein the sequencing reads comprise a coverage of less than 2×, less than 1×, less than 0.50×, less than 0.25×, less than 0.15×, less than 0.10×, or less than 0.05× of a genome of the test subject.

14. The method of claim 3, wherein the sequence information comprises a coverage of between 0.05× and 0.5×.

15. The method of claim 3, comprising determining whether an aneuploidy is due to a meiosis I error or a meiosis II error when the aneuploid chromosome is a meiotic-origin aneuploidy.

16. The method of claim 3, comprising randomly resampling between 2 and 1000 of the sequencing reads, between 3 and 100 of the sequencing reads, between 4 and 50 of the sequencing reads, between 5 and 30 of the sequencing reads, or between 6 and 20 of the sequencing reads.

17. The method of claim 16, comprising computing likelihood distributions of the resampled test subject alleles under at least two competing chromosome number status hypotheses for each of the GWs.

18. The method of claim 3, wherein the GWs are non-overlapping.

19. The method of claim 3, wherein the GWs comprise between 2 and 100000 defined genomic windows, between 3 and 10000 defined genomic windows, between 4 and 1000 defined genomic windows, between 5 and 100 defined genomic windows, between 10 and 75 defined genomic windows, between 20 and 50 defined genomic windows, or between 30 and 40 defined genomic windows.

20. The method of claim 3, wherein a given GW comprises a length of between 5 bases and 1000000 bases, between 10 bases and 100000 bases, between 100 bases and 10000 bases, or between 500 bases and 1000 bases.

* * * * *